(12) United States Patent
Chen et al.

(10) Patent No.: US 10,712,333 B2
(45) Date of Patent: Jul. 14, 2020

(54) SEMICONDUCTOR DEVICE FOR DETERMINING A BIOMOLECULE CHARACTERISTIC

(71) Applicant: Taiwan Semiconductor Manufacturing Company Limited, Hsinchu (TW)

(72) Inventors: Kun-Lung Chen, Hsinchu (TW); Tung-Tsun Chen, Hsinchu (TW); Cheng-Hsiang Hsieh, Taipei (TW); Yu-Jie Huang, Kaohsiung (TW); Jui-Cheng Huang, Hsinchu (TW)

(73) Assignee: Taiwan Semiconductor Manufacturing Company Limited, Hsinchu (TW)

( * ) Notice: Subject to any disclaimer, the term of this patent is extended or adjusted under 35 U.S.C. 154(b) by 0 days.

(21) Appl. No.: 15/994,153

(22) Filed: May 31, 2018

(65) Prior Publication Data

US 2019/0004027 A1    Jan. 3, 2019

Related U.S. Application Data

(60) Provisional application No. 62/525,850, filed on Jun. 28, 2017.

(51) Int. Cl.
| | | |
|---|---|---|
| *G01N 33/487* | (2006.01) | |
| *C12Q 1/6874* | (2018.01) | |
| *G01N 27/414* | (2006.01) | |
| *C12Q 1/6869* | (2018.01) | |

(52) U.S. Cl.
CPC ..... *G01N 33/48721* (2013.01); *C12Q 1/6874* (2013.01); *G01N 27/4145* (2013.01); *G01N 27/4146* (2013.01); *G01N 27/4148* (2013.01); *C12Q 1/6869* (2013.01)

(58) Field of Classification Search
CPC .......... G01N 27/4145; G01N 27/4146; G01N 27/4148; G01N 33/48721; C12Q 1/6874
See application file for complete search history.

(56) References Cited

U.S. PATENT DOCUMENTS

| | | | |
|---|---|---|---|
| 2003/0228603 A1* | 12/2003 | Cload ................ | B82Y 30/00 435/6.11 |
| 2010/0292101 A1* | 11/2010 | So ..................... | C12Q 1/6869 506/16 |
| 2011/0227558 A1* | 9/2011 | Mannion ............ | B82Y 30/00 324/71.1 |
| 2014/0256030 A1* | 9/2014 | Shen .................. | B29C 65/72 435/287.3 |

* cited by examiner

*Primary Examiner* — Dale E Page
*Assistant Examiner* — Quovaunda Jefferson
(74) *Attorney, Agent, or Firm* — Jones Day

(57) ABSTRACT

A semiconductor device includes a circuit layer and a nanopore layer. The nanopore layer is formed on the circuit layer and is formed with a pore therethrough. The circuit layer includes a circuit unit configured to drive a biomolecule through the pore and to detect a current associated with a resistance of the nanopore layer, whereby a characteristic of the biomolecule can be determined using the currents detected by the circuit unit.

20 Claims, 28 Drawing Sheets

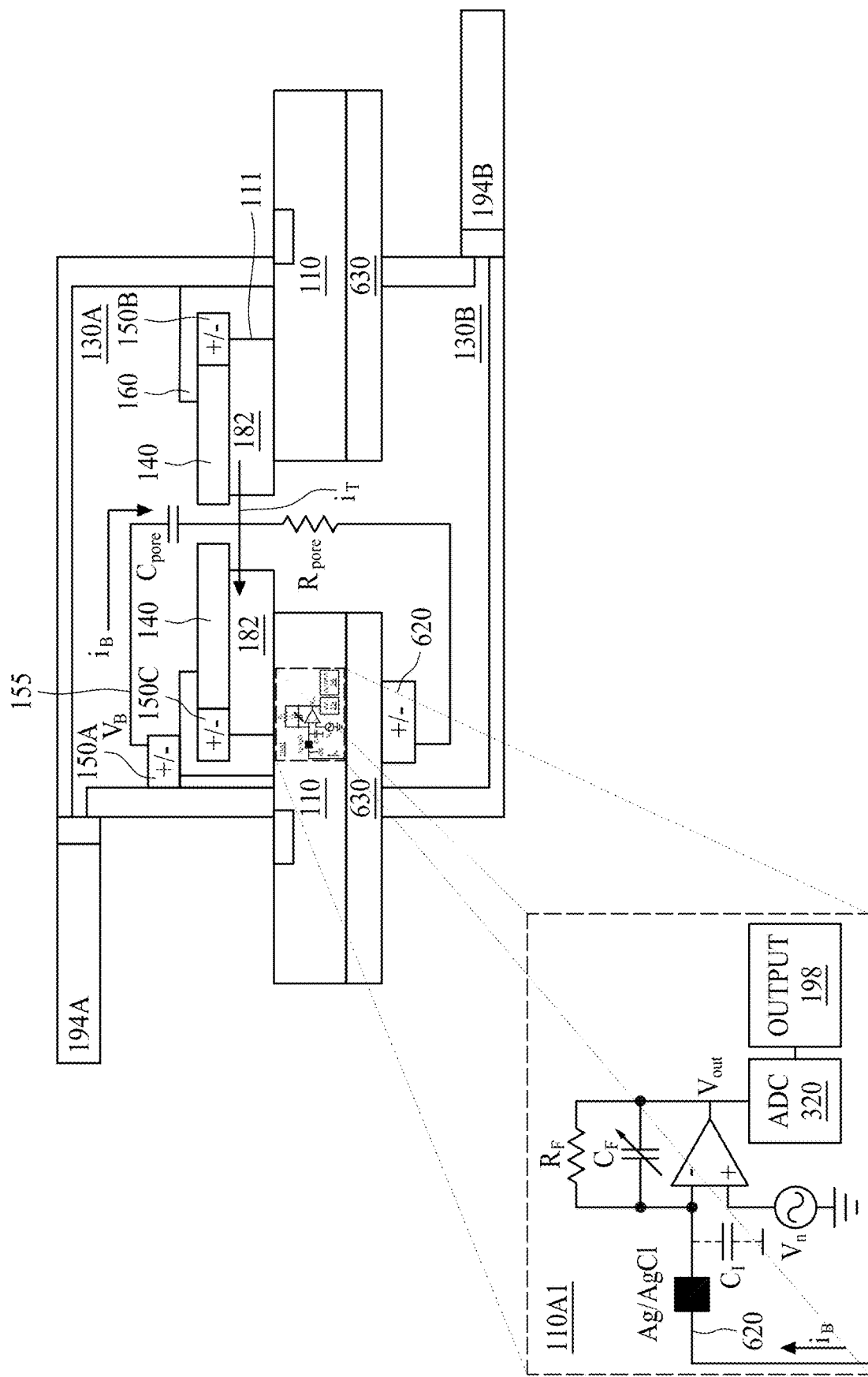

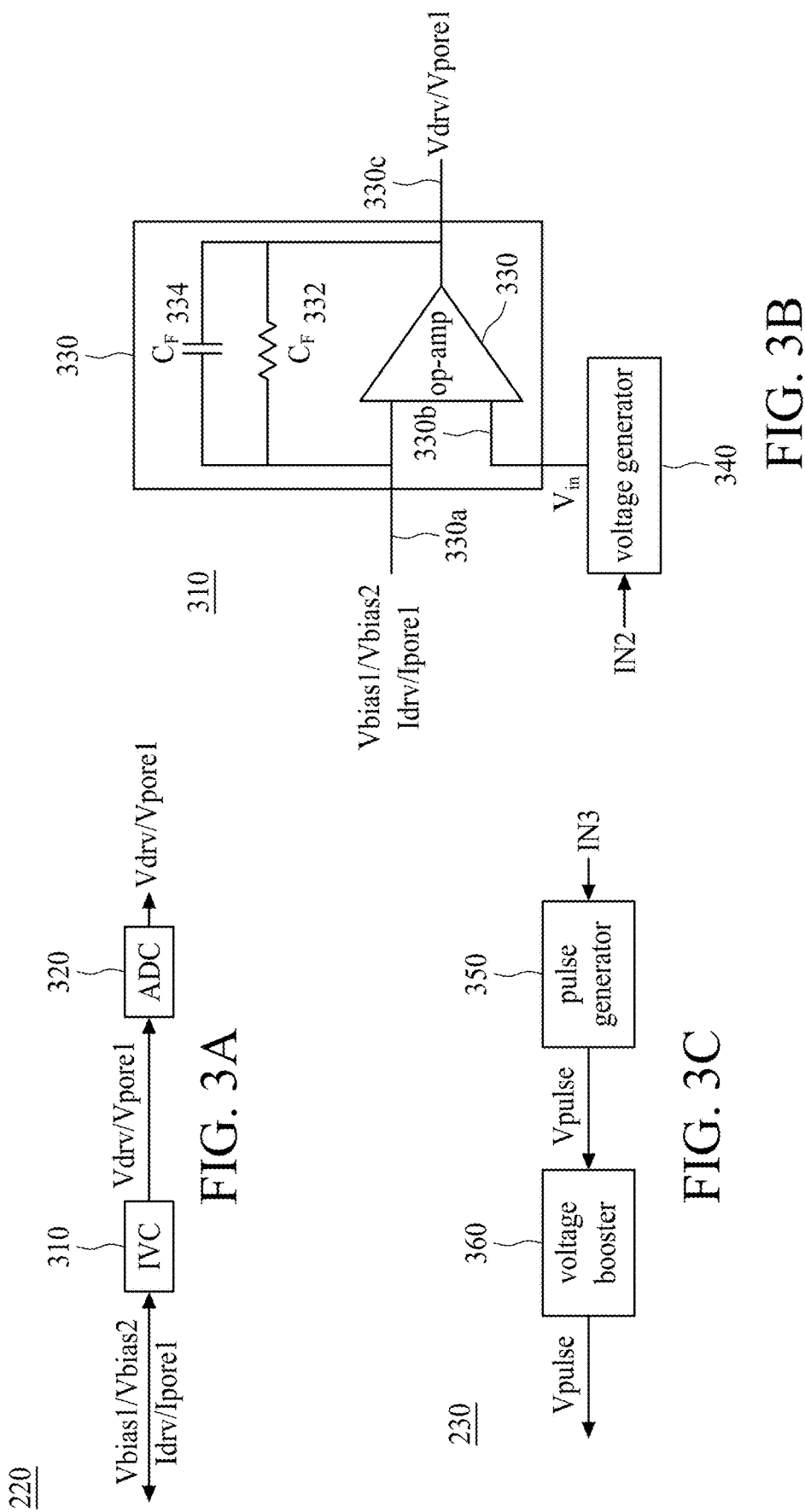

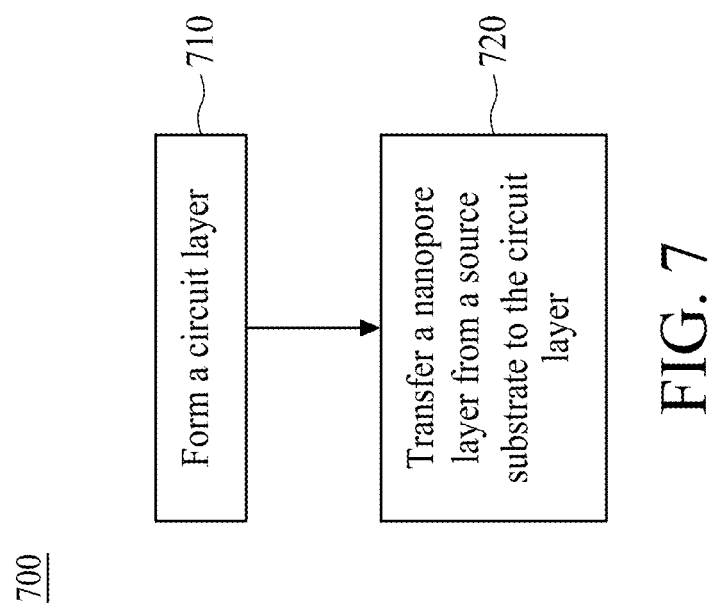

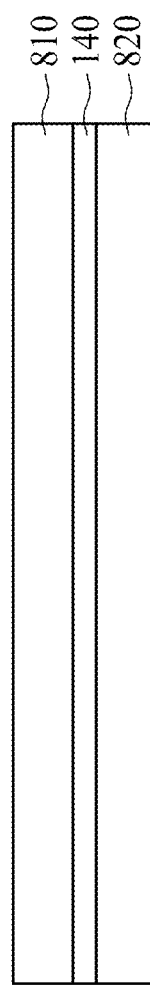
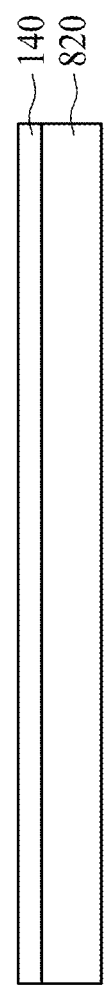
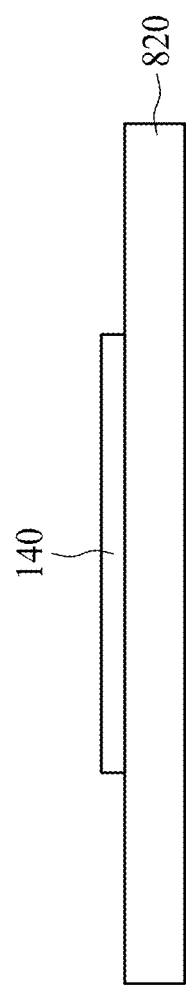

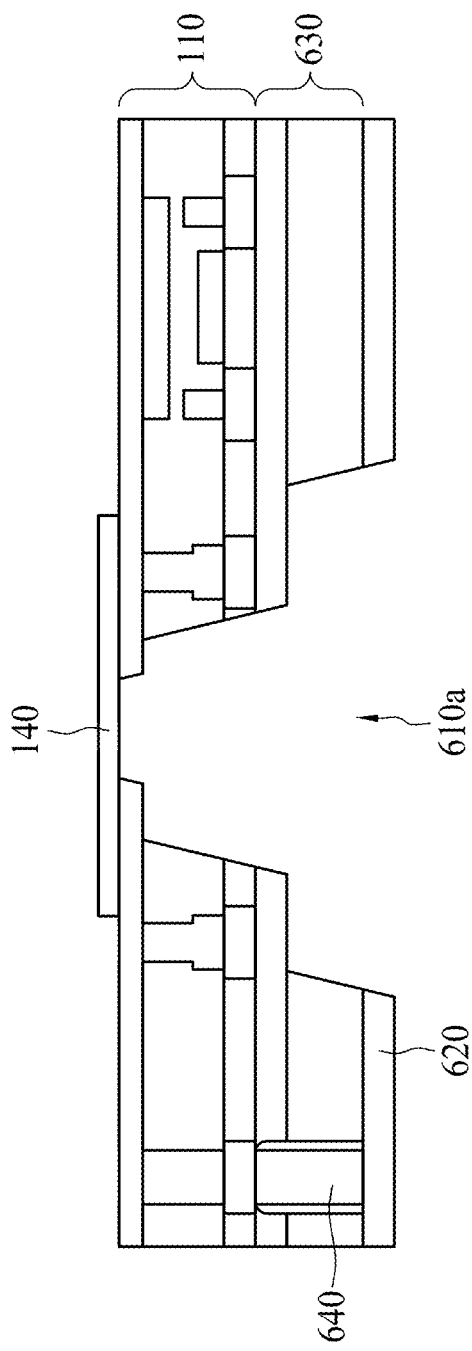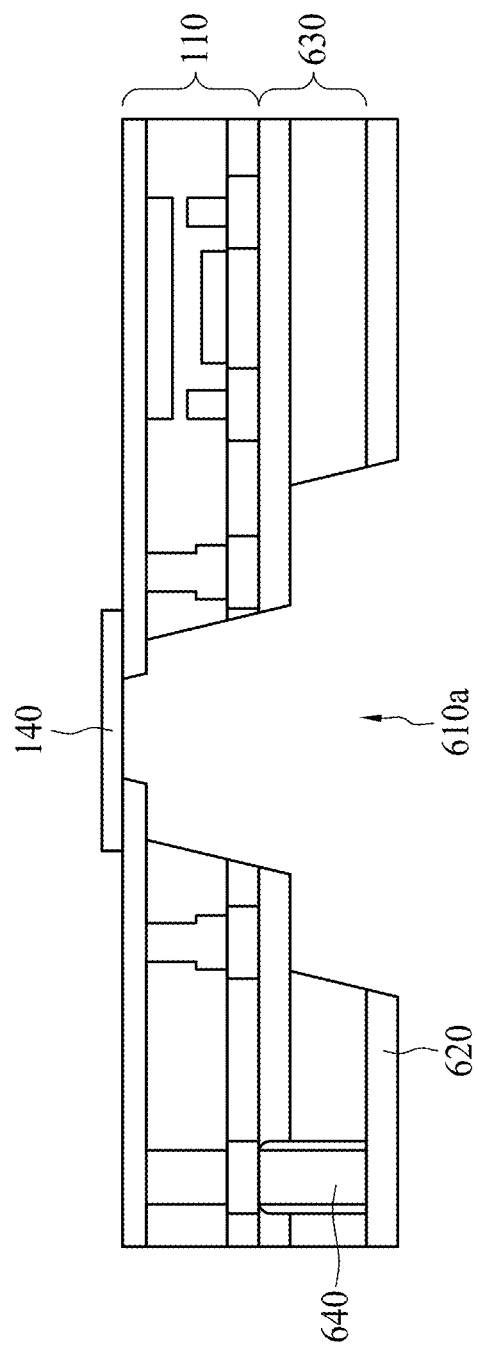

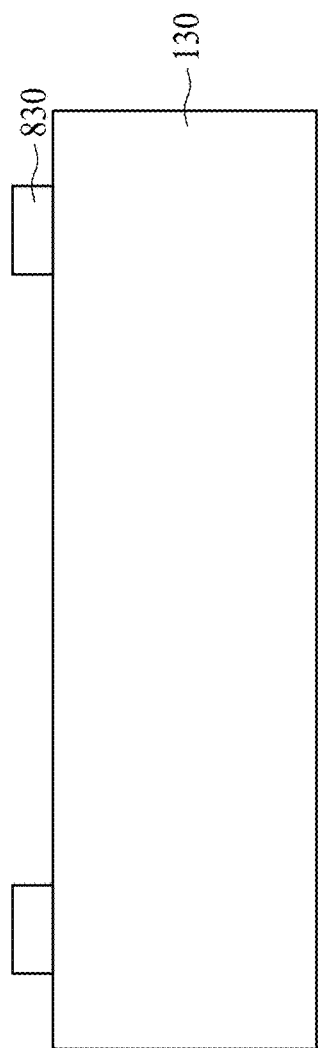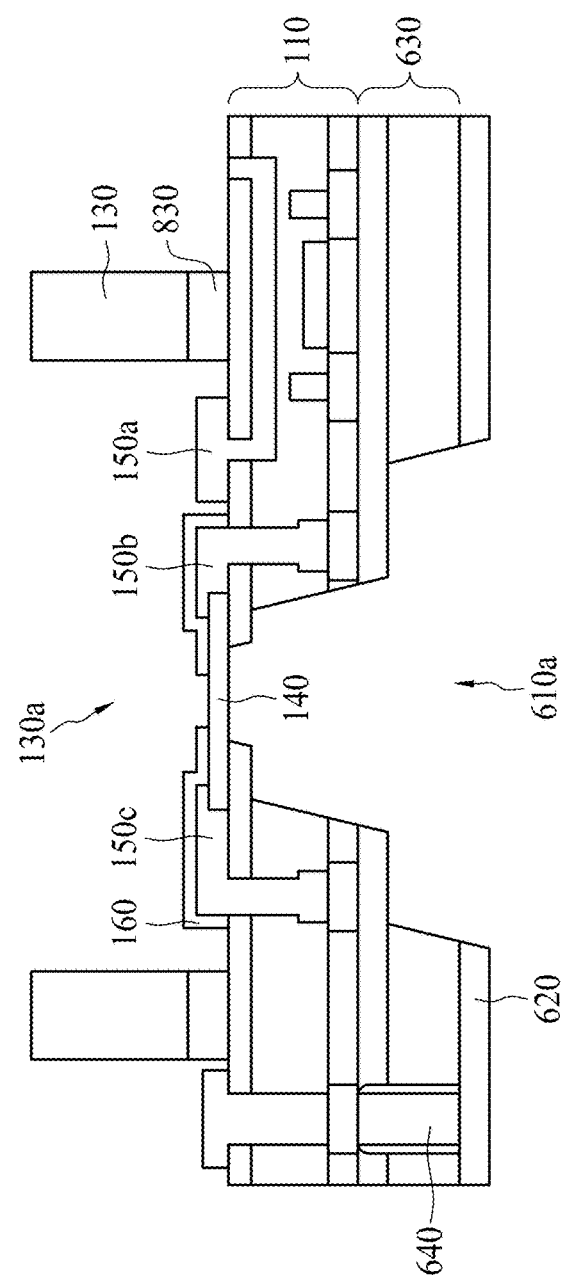

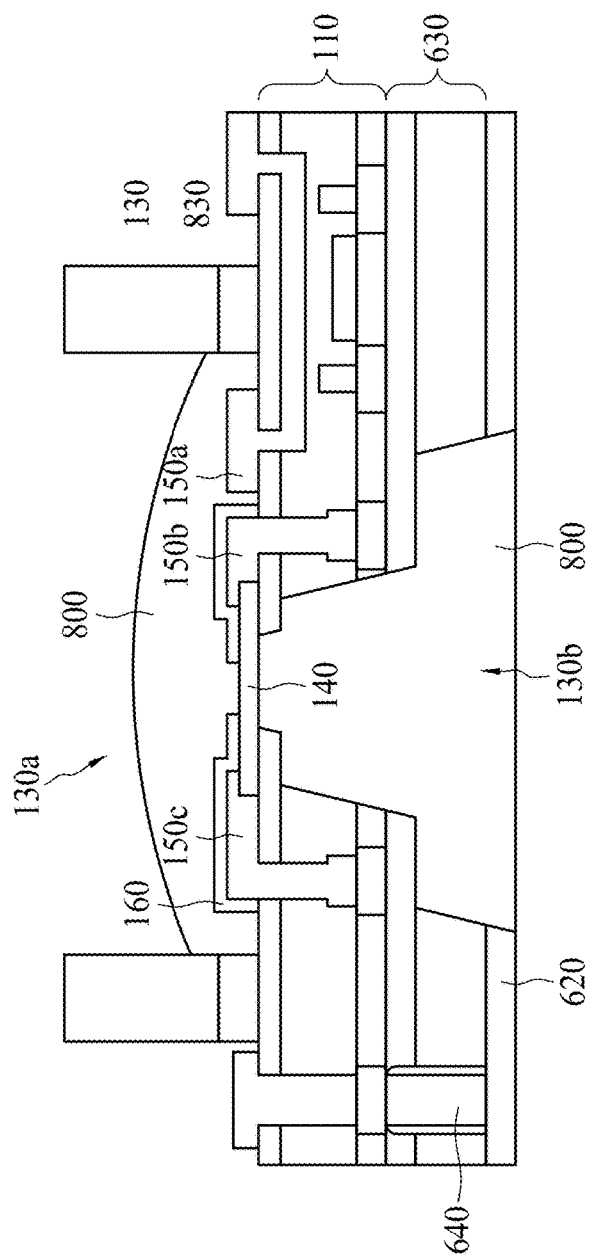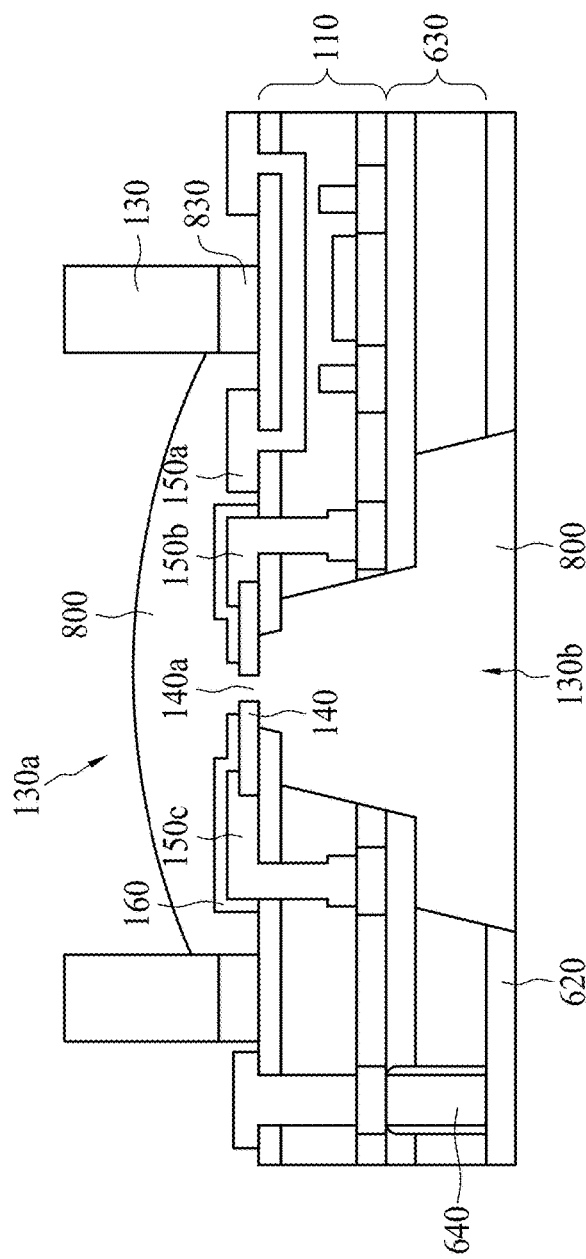

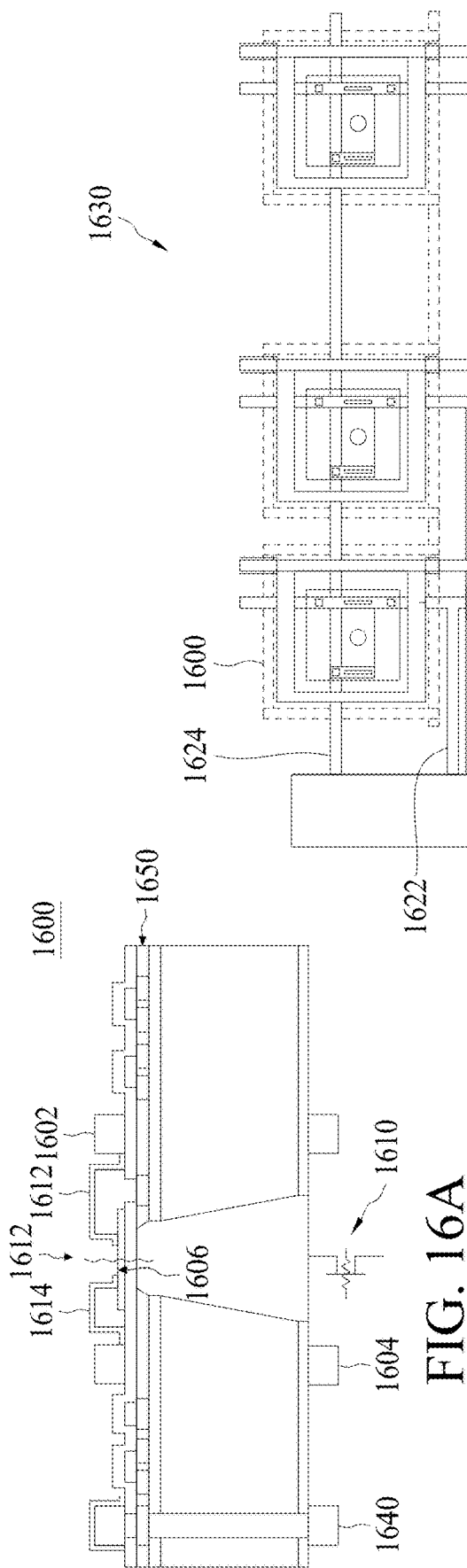
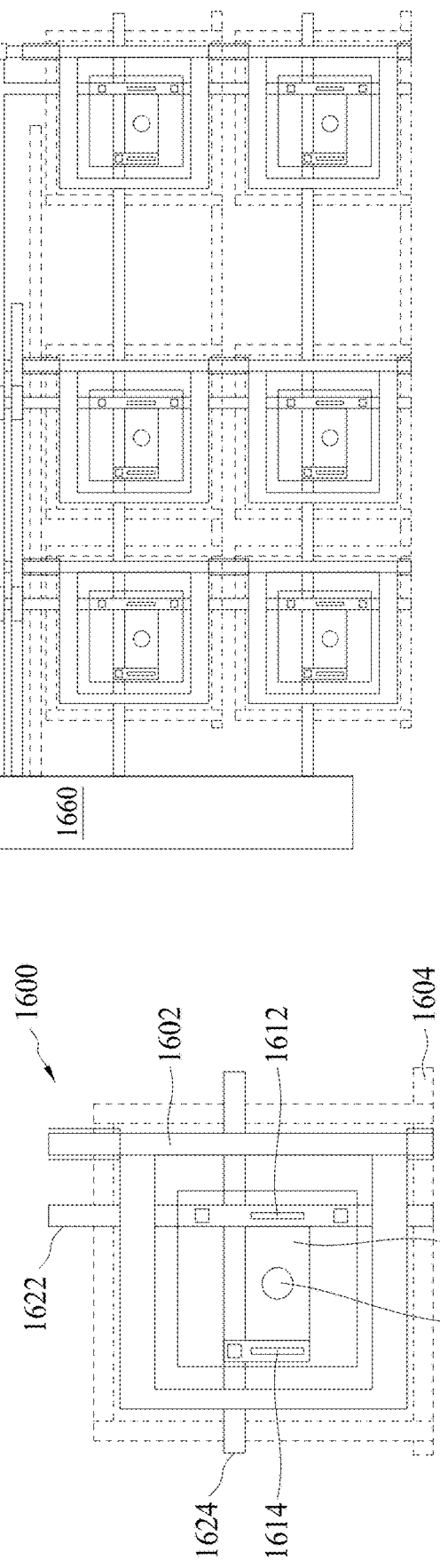
FIG. 16A
FIG. 16B
FIG. 16C

SEMICONDUCTOR DEVICE FOR DETERMINING A BIOMOLECULE CHARACTERISTIC

CROSS-REFERENCE TO RELATED APPLICATIONS

This application claims priority to U.S. Provisional Application No. 62/525,850, filed Jun. 28, 2017, entitled "Integrated Semiconductor Nanopore Biosensor," which is incorporated herein by reference in its entirety.

FIELD

The technology described in this disclosure relates generally to microfluidic applications of Micro-Electro-Mechanical systems (MEMS).

BACKGROUND

Nanopore sequencing is a technique for determining one or more characteristics of a biomolecule, e.g., ribonucleic acid (RNA), deoxyribonucleic acid (DNA) strand, toxins, etc. A biomolecule sequencing device is able to identify characteristics such as the sequence/order of nucleotide bases in order to characterize a DNA strand. In nanopore sequencing a DNA strand, for example, is suspended in a solution and driven through a pore in a nanopore device. As a DNA strand passes through the pore, electrical characteristics (e.g. a resistance, a sensed current, or a sensed voltage) of the nanopore device vary in a deterministic manner as different nucleotide bases, i.e., adenine (A), guanine (G), cytosine (C), and thymine (T), of the DNA strand pass through the pore. Studies have shown that variations in DNA sequences are associated with a range of diseases, such as cancer, cardiovascular disease, and immune system disease. It is important, therefore, to accurately measure characteristics of the nanopore device during the nanopore sequencing in order to accurately characterize the DNA strand.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

FIG. 1D illustrates aspects of an integrated circuit integrated with a semiconductor based biomolecule sensor device in accordance with some embodiments.

FIG. 3A is a functional block diagram illustrating an exemplary driving module in accordance with some embodiments.

FIG. 3B is a functional block diagram illustrating an exemplary current-to-voltage converter in accordance with some embodiments.

FIG. 3C is a functional block diagram illustrating an exemplary pore-forming module in accordance with some embodiments.

FIG. 7 is a flow chart illustrating an exemplary method of manufacturing a semiconductor device in accordance with some embodiments.

FIG. 16A is a cross sectional view illustrating various aspects of a semiconductor based biomolecule sensor device in accordance with some embodiments.

FIG. 16B is a top down view illustrating various aspects of a semiconductor based biomolecule sensor device in accordance with some embodiments.

FIG. 16C is a top down view illustrating various aspects of an array of semiconductor based biomolecule sensor devices in accordance with some embodiments.

DETAILED DESCRIPTION

Figure 1A:
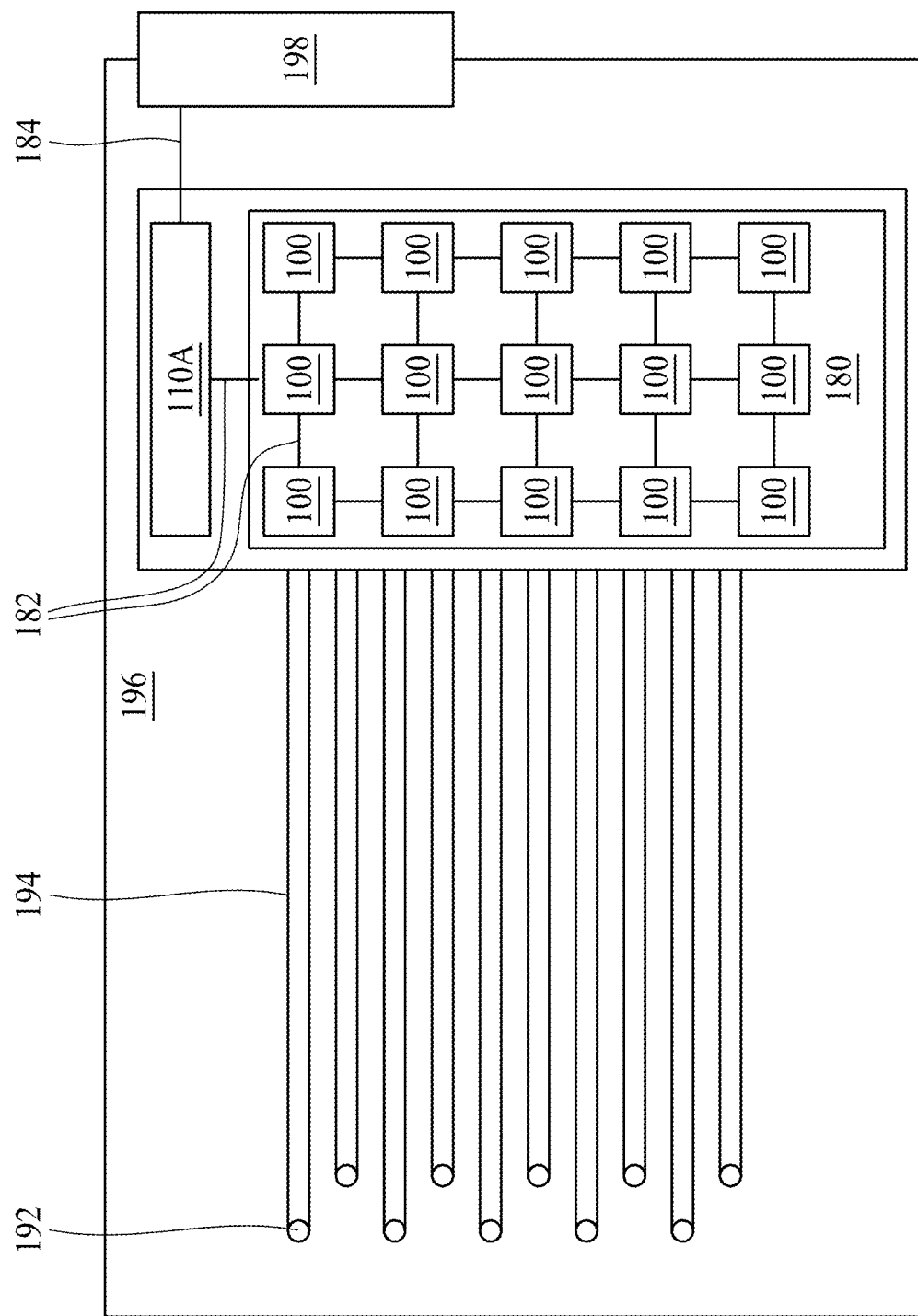
FIG. 1A is a schematic illustration of an exemplary microfluidic device having an array of biomolecule sensors in accordance with some embodiments.

The following disclosure provides many different embodiments, or examples, for implementing different features of the invention. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

Nanopore sequencing of a biomolecule involves passing a biomolecule through a nanopore of a nanopore device, and sensing changes in the nanopore device as the biomolecule passes through the nanopore. A nanopore sequencing device includes a sensing component, typically a nanopore device, and a sequencing component, which may be an external circuit. The external circuit controls the application of voltages across a nanopore device. The external circuit also senses responsive changes in electromechanical characteristics of the sensing component as a biomolecule passes through a nanopore of the nanopore device. Nanopore sequencing can be performed with a sensing device, e.g. a nanopore device, coupled to a remote sequencing device through electrode wires. As variations in electromechanical characteristics of a nanopore device are sensed, an analog signal associated with a change in current or voltage is created. The analog signal thus represents variations in electromechanical characteristics of a nanopore device and thereby characteristics of a biomolecule passing through a nanopore. But as electromechanical devices become smaller and smaller, e.g. on the micrometer, nanometer, or picometer scale, changes in detected currents or voltages are small, and increasingly susceptible to introduced noise. An analog signal describing variations in the electromechanical characteristics of a nanopore device, however, must be accurately conveyed to a sensing circuit in order to accurately characterize a biomolecule passing through a nanopore.

Electric wires are typically used to couple a nanopore senor device to a biomolecule characterization device, which may be a biomolecule detection device for example. But coupled noise and parasitic capacitances may be produced across the electrode wires thereby distorting signal. Thus, longer electrode wires introduce more noise than shorter electrode wires, and biomolecule sequences obtained by sensing electromechanical changes may become inaccurate as a result of noise and distortion introduced by the wires. Thus, by forming sensing circuitry in a semiconductor integrated circuit layer coupled directly to a nanopore sensor, a sensed signal may be converted to a digital form by in situ formed integrated circuitry. The digital signal can then be transmitted off chip without concern for introduced noise and distortion affecting the sensed signals over long distances, so long as the noise level is low enough to distinguish binary highs (e.g., ones or zeros) to binary lows (e.g., zeroes or ones).

Also, traditionally, a semiconductor nanopore is formed by e-beam ion milling. The cost and throughput of e-beam ion milling present substantial hurdles when commercializing a device, and increases the complexity of placing a nanopore device having a pre-formed nanopore such that the formed nanopore is appropriately situated. In order for a nanopore device to be properly situated, a nanopore in the nanopore device may need to be precisely placed such that the nanopore is co-axial with an orifice between two chambers of a semiconductor device. In this way, a nanopore device may function as a membrane covering an orifice separating two solution filed chambers. In this way a molecule may transit from one chamber of to another chamber through the nanopore. Such a semiconductor device may also have an integrated circuit coupled directly to the nanopore device that including pore forming circuitry such that a nanopore device need not be pre-formed, but instead may be formed in situ. Thus, a nanopore device coupled directly to a semiconductor device both minimizes noise and distortion by minimizing the length of a conducting path between a nanopore device and correspond sensing circuitry, while also allowing a nanopore to be formed in a nanopore device in place in precisely the correct location. Also, a nanopore formed in a nanopore device coupled with an integrated semiconductor circuit in accordance with this disclosure creates two measureable signal paths, as described below, which carry two signals that may be compared to increase detection accuracy. For example, as described further below, where a nanopore device is a liquid gated 2D transistor, a first current passes through the nanopore, i.e. in an solution in which the nanopore device is immersed, while a second current flows through the nanopore device itself. Each current is, in part, determined based on the size of the nanopore, and the presence of a biomolecule within the nanopore. In this way, both currents are deterministically affected by the presence of a biomolecule. As different aspects of a biomolecule pass through the nanopore, each having unique effects on the RC characteristics of the nanopore, each current varies proportionally to the changing RC characteristics.

Figure 1B:
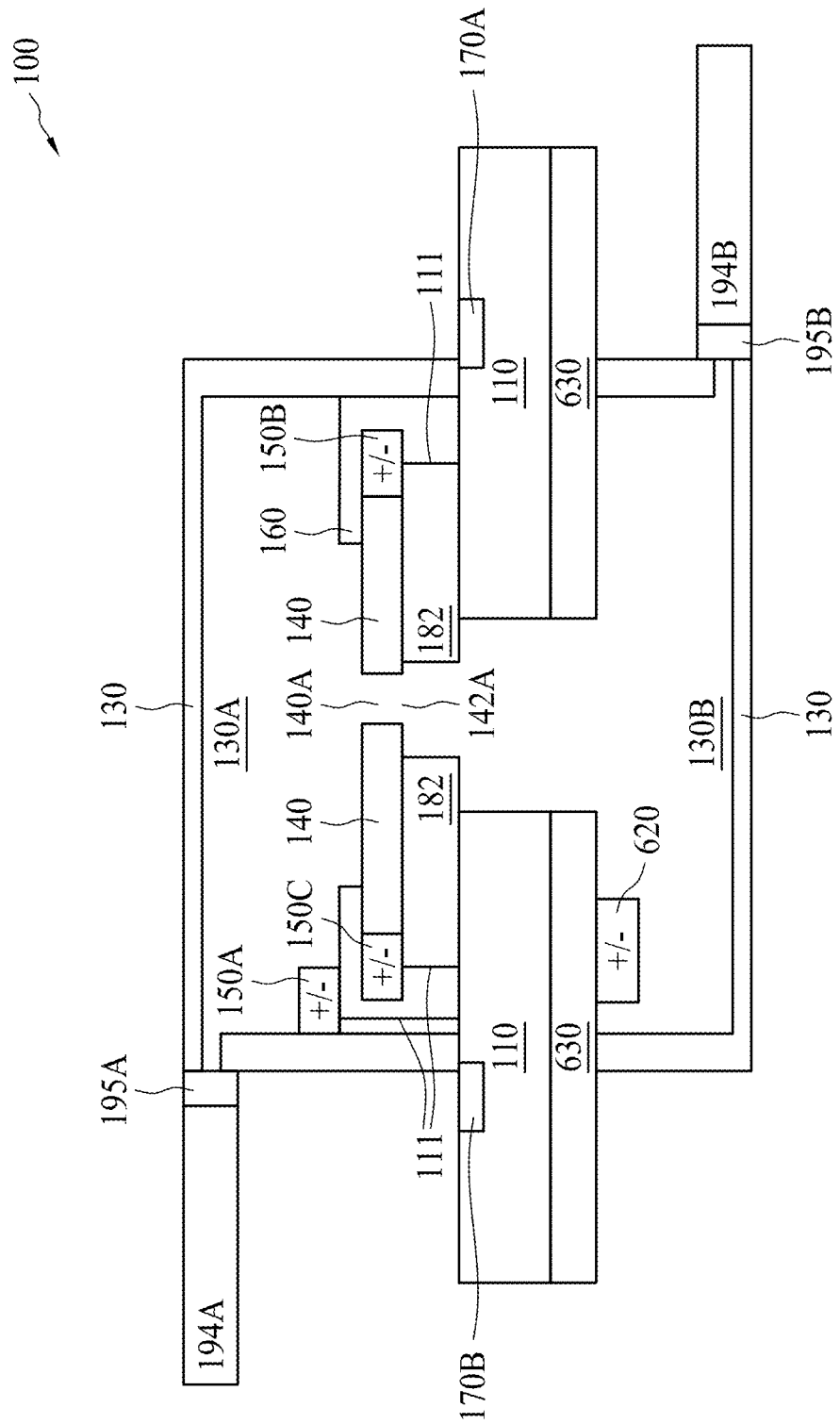
FIG. 1B is a cross sectional view of a semiconductor based biomolecule sensor device illustrating various aspects of nanopore device integrated with an integrated circuit in accordance with some embodiments.
Figure 1C:
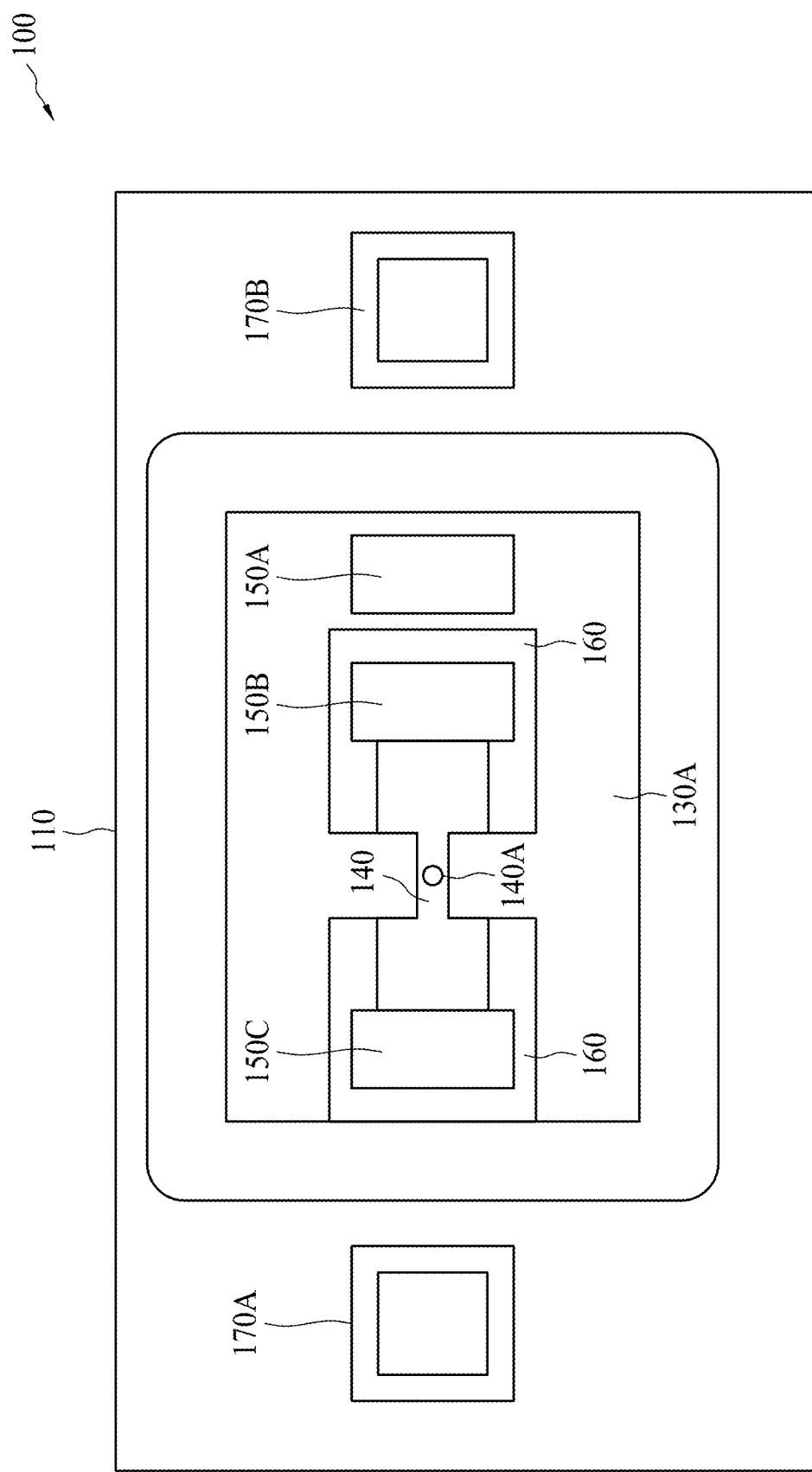
FIG. 1C is a schematic top view illustration of an exemplary semiconductor based biomolecule sensor device in accordance with some embodiments.

FIGS. 1A-1C illustrate various aspects of various embodiments of a microfluidic chip 196. FIG. 1A is an illustration of various aspects of a biomolecule sensing device including an array 180 of semiconductor devices 100 integrated with control circuitry 110A disposed in a microfluidic chip 196. FIG. 1B is a cross sectional view of a semiconductor device 100 illustrating aspects of exemplary semiconductor device 100 with integrated nanopore device 140. In embodiments, semiconductor device 100 is used as a biomolecule sensing cell in a biomolecule detection device. FIG. 1C is a top-down view illustrating aspects of exemplary semiconductor device 100 having an integrated nanopore device 140. FIG. 1D illustrates aspects of an electric circuit of an exemplary biomolecule sensing device, e.g. device 100. In embodiments, microfluidic chip 196 serves as a biomolecule detection device.

Microfluidics device, e.g. microfluidic chip 196, are device that deal with the precise control and manipulation of working fluids while such fluids are geometrically constrained to small, typically micrometer, or smaller, scale. In some applications microfluidic channels employ passive fluid control techniques, e.g. capillary forces, to control the movement of fluids, e.g. the working fluid. In other applications, microfluidic applications apply active microfluidic components, including micropumps and microvalves, e.g. 195A or 195B, to control the movement and direction of flow of working fluids. Other exemplary microfluidic structures include micropneumatic systems in order to handle delivery of external fluid, applied to an interface, to various aspects of a microfluidic system. Such microfluidic structures coordinate and control the movement of small volumes of working fluid (e.g., as small as nanoliters or picoleters) throughout such a system. A microfluidic chip, e.g. 196, is a set of micro-channels etched or molded into a material (glass, silicon, or polymer such as PDMS, for PolyDimethylSiloxane). The micro-channels, e.g. 194, forming the microfluidic chip are connected together in order to achieve the desired features (mix, pump, sort, or control the fluidic environment, e.g. a biochemical environment). Inputs and outputs, e.g. 192, connecting a microfluidic chip to an external environment are created by piercing the chip to create an interface to the macro-world. Through these holes, fluids (or gases) are injected and removed from the microfluidic chip (e.g. through tubing, injectors, syringe adapters, wicks, or by other means passive or active). At the nanometer scale, microfluidics may be referred to as nanofluidics.

MEMS, in its most general form, are miniaturized devices, structures, or systems that are made by employing microfabrication techniques and that integrate electrical and mechanical elements. MEMS are devices, such as nanopore layer 140, formed by microfabrication techniques. MEMS is broad term for describing microscopic devices, and methods of fabricating such devices, which may range in dimensions from hundreds of micrometers down to the nanoscale where MEMS encompasses nanoelectromechanical systems (NEMS). An application of MEMS is in microsensors, e.g. semiconductor device 100, which may be integrated with microfluidic systems, that are capable of detecting the presence of target substances in small (microliter or less) volumes of liquid.

A characteristic of a biomolecule can be determined using a semiconductor device, such as semiconductor device 100, or an array 180 of semiconductor devices 100. One semiconductor device 100, or an array 180 of semiconductor devices 100, are disposed in a microfluidic chip 196. Microfluidic chip 196 includes one or more micro-channels 194 coupling one or more inputs 192 to the one or more micro-channels 194 for carrying small volumes of working fluids to an array 180 of one or more semiconductor devices 100. Working fluids include electrolytic solutions provided to various first chambers 130A or second chambers 130B of the semiconductor devices 100. Working fluids may also carry one or more biomolecules from inputs 192 to the one or more semiconductor device 100 chambers 130A, 130B. Each semiconductor device 100 in an array of semiconductor devices 180 (which may be only a single device 100) is coupled via signal carrying conductors, or interconnections, 111 to one or more semiconductor circuits 110A (while FIG. 1A illustrates only a single semiconductor circuit 110A, it is to be understood that circuit 110A may be a plurality of distinct circuits coupled respectively to a plurality of semiconductor devices in array 180, or circuit 110A may be disposed in a single semiconductor layer 110, and comprise a plurality of subcircuits associated with each of the semiconductor devices 100, or semiconductor circuit 110A may be a single circuit for controlling each semiconductor device 100 in array 180). A circuit layer 110 may be formed on a wafer, e.g. wafer 630.

In determining a characteristic of a biomolecule, e.g., sequence/order of nucleotide bases of a strand of DNA, first and second chambers 130A, 130B of a semiconductor device 100 are filled with a chemical solution, e.g. provided through microchannels 194A or 194B. For example, a DNA strand is provided in a chemical solution to a first chamber 130A via microchannel 194A. Fluid provided to a first chamber 130A may pass through a micro-valve 195A which controls the transfer of liquids into first chamber 130A (alternatively micro-valve 195A is omitted and other structures in the microfluidic chip (not illustrated) control the flow of liquids through microchannel 194A. Next, a DNA strand (not particularly illustrated) is electrophoretically driven from a first chamber 130A to a second chamber 130B through a pore 140A in a nanopore device 140 by a sensing device (e.g., a CMOS control circuit 110A formed in semiconductor layer 110). One or more characteristics of the DNA strand are detected as the DNA strand passes through the pore 140A.

Electrophoresis refers to causing particles to migrate through a stationary medium, like a solution, under the influence of an applied electric field. An applied electric field may be provided by immersed electrodes, e.g. electrodes 150A, 620. In one example, a pair of electrodes 150A, 620 are inserted into the chemical solutions contained in respective first and second chambers 130A, 130B and the sensing device (e.g. circuit 110A) applies a drive voltage across the electrodes 150A, 620. As the DNA strand passes through the pore 140A, the sensing device (e.g. circuit 110A) detects a drive current through the electrodes 150A, 620 (which are electrically connected through the chemical solutions forming a circuit loop 155, as illustrated in FIG. 1D). The drive current detected is a function of the associated drive voltage and a corresponding change in the RC characteristics of the nanopore device 140 (e.g., changes in $R_{pore}$ or $C_{pore}$), where different biomolecules, e.g. nucleotide bases (A, T, C, G), are known to have different deterministic effects on the RC characteristics of a nanopore device as they pass through the nanopore. For example, DNA a sequence may be identified by determining changes in resistance of a nanopore sensing changes in a drive current detected by the sensing device. A sensing device, e.g., may sense such changes in current using integrated circuitry, e.g. 110A1.

Embodiments of the present disclosure address the deficiencies of known approaches by coupling a nanopore biosensor device with a semiconductor integrated circuit, e.g. silicon CMOS technology, which includes sensing circuitry (e.g. 110A1). Such sensing circuitry may be formed by a suitable semiconductor manufacturing process for forming integrated circuits within a semiconductor layer, e.g. 110, of a semiconductor device. The semiconductor process includes forming a semiconductor device to support a nanopore device, e.g. nanopore layer 140. A nanopore layer, e.g. 140, is formed and disposed upon the semiconductor device, e.g. 100, using known microelecromechanical systems (MEMS) techniques.

In embodiments, a nanopore device 140 is coupled onto a semiconductor layer 110, or onto an insulator layer 182 formed over a semiconductor layer 110. Integrated circuit layer 110 has an integrated circuit (e.g, 110A, 110A) configured to sense changes in currents and voltages (e.g. $i_B$ or $V_B$) across such a nanopore layer, e.g. 140. In this way, a length of a conductor coupling a nanopore device to a sensing circuit is minimized and noise is reduced. An integrated sensing circuit 110A1 converts a sensed analog signal, e.g. $i_B$, to a digital word for transmission to an external biomolecule characterization device via output 198. Since all electrical components are integrated with a nanopore sensor device, e.g., a SNR is greatly improved due to the elimination of noise that incurs when long interconnect wire, or conductor, couples a sensing device with its corresponding sensing electronics. Such a biomolecule sensing device, e.g. semiconductor device 100, is thus configured to detect and encode variations in sensor currents or voltages into a digital signal transmitted to a characterization device in order to detect a particular biomolecule.

When a biomolecule passes through a nanopore, aspects of the biomolecule are sensed by a sensor circuit that includes either an electrolytic fluid passing through a nanopore, 140A, or that includes a nanopore device 140. Known semiconductor based or organic nanopore devices typically have thicknesses that are substantially larger than single biomolecule targeted for detection, and therefore have low resolution for sensing aspects of a biomolecule, e.g. a nucleotide. However, 2D transistors, such as a graphene nanoribbon, may be utilized as nanopore devices 140. Such a 2D transistor may have a thickness on the order of a nucleotide, and are therefore able to resolve individual nucleotides with enhanced accuracy.

Thus, a 2D transistor nanopore layer, e.g. 140, is disposed upon a surface of semiconductor device 100 and coupled by interconnections 111 to an integrated circuit layer 110 formed below the nanopore layer. As described further below, a 2D transistor disposed on and electrically coupled to a semiconductor device may pass a current between two electrodes coupled to the nanopore layer, for example, when a voltage is applied between solutions in contact with opposing surfaces of a 2D transistor, e.g. 140. Applying such a voltage may be referred to as liquid-gating such a 2D transistor. The voltage applied to solutions in chambers 130A and 130B act like a gate signal causing conduction along the 2D transistors length (e.g. $i_T$ flowing perpendicular to $i_B$).

The semiconductor device 100 and nanopore 140 are disposed within a solution in a fluid chamber 130 such that the nanopore layer separates a fluid chamber 130 into a portion above the nanopore layer 130A and a portion below the nanopore layer 130B. In this way, the upper and lower portions are separated by the nanopore device 140 while allowing biomolecules molecules to pass between the chambers through the nanopore 140A. In this way a resulting fluid chamber 130 includes the portion above the nanopore layer 130A and the portion below the nanopore layer 130B and a relatively small portion defined by the nanopore 140A itself. A fluid chamber contains a solution that suspends biomolecules. In embodiments a bias voltage (e.g., $V_B$) is applied between the solution in the portion above the nanopore device 130A and the solution in the portion below the nanopore device 130B. As a biomolecule passes through the pore 140A, a current ($i_B$) passing through the nanopore 140A changes as different parts of a target molecule passes through the nanopore 142A. For example, different nucleotides of a DNA strand may change the resistance encountered by a current $i_B$ as it passes through the nanopore. The passing biomolecule also alters the source to drain RC characteristics of such a liquid gated 2D transistor 140, thereby altering a current $i_T$ passing through the nanopore device perpendicular to $i_B$ (i.e., through the 2D transistor).

In embodiments, a device 100 also eliminates the need for traditional e-beam ion milling by allowing in situ, i.e. in place, nanopore 140A formation. That is, an unformed nanopore device, e.g., such a 2D graphene nano-ribbon transistor may be disposed upon a semiconductor device (e.g. 100) and coupled to metal contacts (e.g. 150B, 150C) that are integrated with portions of integrated circuit (e.g. 110A, 110A1). Then the nanopore device (e.g. 140), or layer, may be formed by creating a nanopore (e.g. 140A), or a pore, in the 2D transistor (e.g. 140). Forming and disposing a nanopore layer (e.g. 140) on a semiconductor device may be accomplished according to any suitable technique, the details of which are beyond the scope of this disclosure.

A 2D transistor, such as 140, may be a graphene nanoribbon 2D transistor. Graphene is essentially a single atomic layer of graphite that is capable of excellent conduction that may vary based on a translayer (i.e transmembrane) applied voltage (akin to a transistor with an applied gate voltage). Graphene is an allotrope of carbon, typically a dielectric, that includes tightly bonded carbon atoms. Because graphene's width is on the order of one atomic unit biomolecules passing through it may be resolved at the atomic level and so may be detected at a higher resolution. A nanopore, e.g. 140A, may be formed in a graphene layer, e.g. 140, by causing a forming voltage to be applied across the width of a graphene nanoribbon, e.g. perpendicular to the length of the 2D transistor. When voltage is applied in this manner, the unformed graphene nanoribbon layer initially acts like a dielectric. Such applied voltage eventually causes leakage current perpendicular to the length of the nanoribbon thereby breaking down the dielectric material of the 2D transistor in a localized area until a pore, e.g. 140A, is formed in the localized area, e.g. a desired area over orifice 142A, thereby allowing current to pass through the now formed nanopore device. Once formed, the size of the pore, e.g. 140A, may be enlarged by appropriate voltages as discussed further below.

In embodiments, a formed nanopore layer 140 with nanopore 140A coupled to an integrated sensing circuit, e.g., 110A, formed in semiconductor layer 110, is able to sense aspects of a biomolecule that passes through pore 140A in the nanopore layer 140. In embodiments a plurality of integrated semiconductor nanopore devices 100 are configured in an array 180 of semiconductor devices with integrated nanopores 100, each including a nanopore 140A and each may be electrically separated from each other semiconductor device 100, or cell, with integrated nanopore. By electrically separating of each nanopore 140A in an array 180, each nanopore 140A coupled to each semiconductor device 100 can be electrically formed independently, thus the size of each individual nanopore 140A can be individually tailored as desired under reliable controls using electrional methods.

Electrical formation of a nanopore 140A may occur directly in a solution, as described herein, by first breaking down the dielectric, e.g. the carbon lattice of a graphene nanoribbon, of the nanopore layer 140 using relatively high voltages and then soaking the device with relatively low voltages to enlarge the nanopore to a desired size. Thus, each electrically separated nanopore 140A in an array 180 may be addressed individually, and can individually and concurrently sense biomolecules disposed in each respective semiconductor device chamber (e.g., 130A, 130B). The size of each nanopore 140A can be formed individually and controllably to an intended size by integrated circuitry 110A.

Exemplary, non-limiting, nanopore device structures are based on 2D transistors of either graphene nano ribbon 2D transistors or MOS2 2D transistors. In any case, both the ion current ($i_B$) and transistor source/drain current $i_T$ (e.g. a currently flowing along the length of the transistor between electrodes 150B, 150C, and perpendicular to $i_B$) may be measured independently of each other by the integrated circuit 110A within the formed semiconductor device circuit layer 110. As a result, noise is significantly reduced by amplifying and digitizing a sense signal (e.g. $i_B$ or $i_T$) locally without large noise interference from outside the devices or from lengthy electrodes. The particular mechanisms for forming and transferring suitable 2D transistors are known in the art and need not further be discussed.

Systems and methods as described herein in various embodiments include a semiconductor device, e.g., semiconductor device 100 in FIG. 1, with a circuit 110A configured to sense a current associated with resistances associated with a biomolecule sensed by such a semiconductor device. By integrating a nanopore biosensor (e.g. 140) with a semiconductor device (e.g. 110), e.g. silicon CMOS technology integrated with a nanopore, the overall semiconductor device 100 minimizes electrical separation between the nanopore sensor 140 and the sensing electronics 110A. This enables a higher signal to noise ratio (SNR) over known semiconductor nanopore devices by eliminating long interconnection wires from the signal path. Sensing a signal from a nanopore biosensor in accordance with this disclosure allows the sampled signal to be converted to a signal encoded with a relatively lossless signal protocol, such as standard digital signals.

The example semiconductor device 100 includes a circuit layer 110 and a first chamber 130A. The first chamber 130A is above the circuit layer 110 and is defined by a chamber wall 130. Disposed in the first chamber 130A is a nanopore layer 140, and an insulating layer 160. The chamber wall 130 is formed, or disposed, on the circuit layer 110, such as by bonding the chamber wall 130 to the circuit layer 110 with the use of an adhesive. The chamber wall 130 defines a first chamber cavity 130A therein configured to receive a chemical solution (not particularly illustrated here, but see solution 800, e.g. FIG. 8T-8U). The chamber wall 130 may, for a non-limiting example, have a length of about 20 μm and a width of about 20 μm. The chamber wall 130 may be formed, for example, of a silicon cap bonded to the semiconductor device 100 surface. The chamber wall 130 is capable of retaining an ionic solution that allows conduction. The ionic solution may be, in embodiments, KCL. The upper chamber may be a cis chamber, and may have a negative voltage applied relative to a corresponding trans chamber. It will be appreciated that embodiments in accordance with this disclosure may include chamber cavities defined by chamber walls of varies sizes dictated by design considerations. Examples of materials for the chamber wall 130 include, but are not limited to, Si, Ge, ceramic, quartz, glass, silicon, or polymer such as PDMS, for PolyDimethylSiloxane and the like.

Semiconductor device 100 may also include a second chamber 130B formed beneath and through the circuit layer 110, and may in part be defined by a cavity formed by surfaces formed within the circuit layer 110, or the second chamber 130B is formed by a second cap bonded to an opposite surface than the surface defining the first chamber 130A. The second chamber 130B is also configured to retain an ionic fluid, and may form a trans chamber and may have a positive polarity applied relative to the cis chamber). And in other embodiments, first chamber 130A forms a trans chamber and the second chamber 130B forms a cis chamber.

In embodiments, the nanopore layer 140 is disposed in the first chamber cavity 130A upon the circuit layer 110 and has first and second end portions and an intermediate portion between the first and second end portions. The nanopore layer includes a pore 140a there-through formed in situ (or pre-formed). The intermediate portion of the nanopore layer 140 may take a variety of forms, for example in one embodiment it may have a 2D area formed of a first length of about 100 nm to about 160 nm and a second length of about 80 nm. The pore 140a has a diameter/width of, e.g., about 2.0 nm and extends through the nanopore layer perpendicular to the 2D area. In an embodiment, the nanopore layer 140 is ribbon-like shaped and includes a monolayer, e.g., about 1 nm thick, graphene. In an alternative embodiment, the nanopore layer 140 includes MoS2, MoSe2, WS2, WSe2, other suitable monolayer material, a dielectric material, such as Si3N4, an oxide-based material, such as Al2O3, or a combination thereof. The nanopore layer 140 may be a 2D transistor, for example a graphene nanoribbon field effect transistor, which forms a membrane and exhibits conduction along its length when a liquid-gating voltage is applied across the membrane (e.g. a voltage between a trans and cis chamber 130A, 130B separated by a nanopore device 140 layer).

A first electrode layer 150A is disposed in the first chamber cavity 130A and is formed over the circuit layer 110. The first electrode layer 150A includes metal resistant to corrosion/oxidation in the chemical solution. Examples of such metal include, but are not limited to, silver, gold, platinum, other corrosion/oxidation-resistant metal, and an alloy thereof.

Additional electrode layers 150B, 150C are disposed in the first chamber cavity 130A, are formed over the circuit layer 110, and are coupled to first and second end portions of the nanopore layer 140, respectively. Layers 150B and 150C may be electrically isolated from an ionic solution within chamber 130A by an insulation layer 160. Electrode layers 150B, 150C may have a different material than the first electrode layer 150B. Examples of materials for the electrode layers 150B, 150C include, but are not limited to, copper, aluminum, titanium, tungsten, other conductive material, and an alloy thereof.

The insulating layer 160 covers the electrode layers 150B, 150C and is configured to prevent exposure of the electrode layers 150B, 150C to the chemical solution retained in chamber 130A by chamber wall 130. The insulating layer 160 further covers the first and second end portions of the nanopore layer 140. The insulator layer 160 covering the first and second end portions of the nanopore layer 140 may also prevents biomolecules passing through the pore 140A from contacting portions the nanopore layer 140, which undesirably alter a resistance of the nanopore layer 140.

The semiconductor device 100 is configured to act in concert with an external device such as a biomolecule characteristic-identifying device (not particularly illustrated), e.g., during a biomolecule sequencing. During such a biomolecule sequencing, a biomolecule characteristic-identifying device may be part of a microfluidic device, e.g. microfluidic chip 196, into which the semiconductor device 100, or an array 180, is inserted. The semiconductor device 100 provides one or more biomolecule characteristics based on electrical characteristics sensed by the combination of nanopore sensor device 140 coupled to integrated circuit layer 110. As illustrated in FIGS. 1B, 1C, the semiconductor device 100 further includes a pair of conductive pads 170A, 170B which enable connection to external circuits. Pads 170A, 170B may couple exemplary circuits 110, 110A, 110A1 to output 198, which provides an output to an external device.

Structures depicted in FIG. 1C are integrated with circuitry (aspects 110A1 of which are illustrate in FIG. 1D) in underlying layers. Such circuitry may be formed in circuit layer 110. Circuit layer 110 may, for example, include semiconductor device integrated circuits, e.g., portions of which are depicted in FIG. 1D. Circuit portion 110A1 for example includes a sensing portion comprising an amplifier configured in voltage follower mode (as depicted). One of skill will appreciate that a voltage follower will convert variations in $i_B$ to a voltage, $V_{out}$, provided with sufficient current $i_{out}$ to supply follow-on stages while allowing for low input currents in e.g. $i_B$. Circuit portion 110A1 may include additional stages, such as an analog to digital converter 320 (ACD) thereby providing a digital signal to output 198 (e.g. in embodiments via pads 170A, 170B, not particularly depicted in FIG. 1D). It will be appreciated that the semiconductor integrated circuit depicted by the schematic in FIG. 1D is only intended to illustrate the integration of semiconductor circuitry in layer 110 with nanopore device 140, and additional sensing and control circuitry may also be formed in semiconductor layer 110 as needed.

Figure 2A:
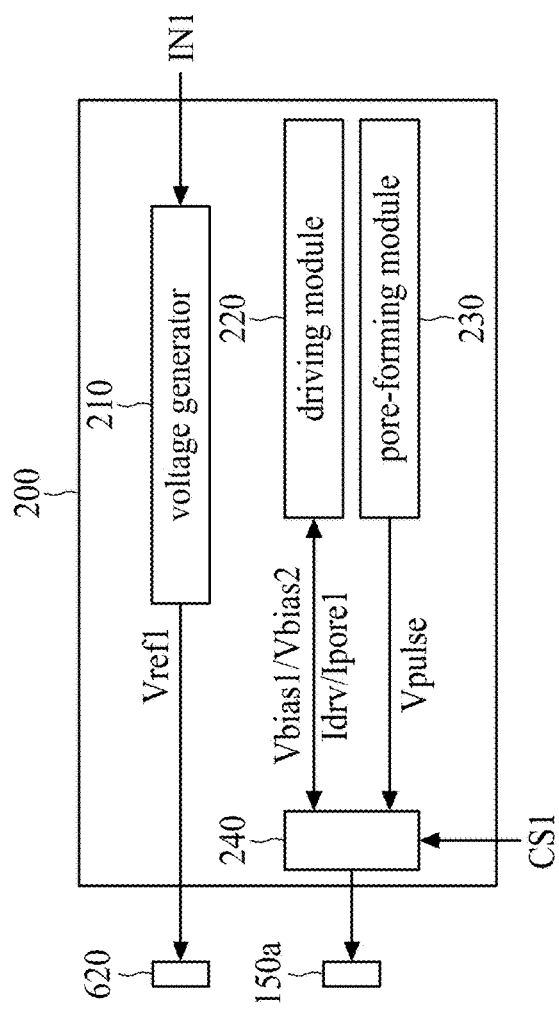
FIG. 2A is a functional block diagram illustrating an exemplary first circuit connected to electrode layers in accordance with some embodiments.

FIG. 2A is a functional block diagram illustrating an exemplary first circuit 200 connected to the first electrode layer 150A in cavity 130A and a second electrode layer 620 disposed in a second cavity 130B opposite the nanopore layer 140 from cavity 130A, as discussed above.

The first circuit 200 is configured to apply a drive voltage (e.g. $V_{bias1}$) across the electrode layers 150A, 620 for driving a biomolecule through the pore 140A. In embodiments, first circuit 200 is further configured to also detect a drive current ($i_{drv}$) through the electrode layers 150A, 620 that is associated with both a drive voltage and corresponding RC characteristics of a nanopore layer, e.g. 140. Alternatively, drive module 220 may alternate between a drive voltage, e.g. $V_{bias1}$, and a sensing voltage, $V_{bias2}$, thereby first driving a biomolecule by applying $V_{bias1}$ and then sensing a pore current ($i_{pore1}$) by applying a second bias voltage $V_{bias2}$. In embodiments $V_{bias2}$ may be the same as, or different than, $V_{bias1}$. As a biomolecule passes through the nanopore 140A, the RC characteristics of the nanopore device 140, as experienced by a current $i_B$ passing through a pore, e.g. 140A, vary causing the current to increase and decrease in a measurable and deterministic fashion. One or more characteristics of the biomolecule may be determined by sensing changes in drive currents ($i_{drv}$) detected by the first circuit 200 while a drive voltage is applied between terminals 150A, 620.

As described below with respect to the manufacture of the semiconductor device 100, the first circuit 200 further configured to form the pore 140A and to measure the diameter of the pore 140A after initially formed. When first disposed above a circuit layer 110, a nanopore layer 140 is initially unformed (not pre-formed), meaning no nanopore has yet been formed. Circuit 200 enables in situ pore formation of a pore 140A in nanopore layer 140. Once a nanopore 140A is formed in nanopore layer 140, nanopore layer 140 is referred to as a formed nanopore layer.

A pore may be formed in an unformed nanopore layer 140 by applying sufficient voltage across the nanopore layer, e.g. between first chamber 130A and second chamber 130B, to cause a dielectric breakdown of the nanopore layer 140 dielectric material (e.g. carbon in graphene form). This dielectric breakdown in an exemplary graphene 2D transistor 140 will cause a predictable increase in current $i_B$ through nanopore layer 140 when a pore 140A is formed. As further voltage is applied, a pore 140A will enlarge causing further predictable current increases as the pore 140A diameter increases. As will be appreciated, once a nanopore 140A is formed, the nanopore layer 140 RC characteristics will change in a predictable manner as a biomolecule passes through a formed pore 140A in a nanopore layer 140.

Pore 140A is dimensioned to a desired size. To form the nanopore 140A, the first circuit 200 is configured to apply pore-forming pulses $V_{pulse}$ across the electrode layers 150A, 620 to form the pore 140A in the nanopore layer 140. The first circuit 200 is further configured to detect a diameter of a formed pore 140A by applying a pore voltage across the electrode layers 150A, 620. The first circuit is further configured to detecting a pore current ($i_{pore}$) through the electrode layers 150A, 620 that is associated with a pore voltage and a corresponding resistance of the nanopore 140A. A diameter/width of the pore 140a may be estimated using the pore currents detected by the first circuit 200. In this way the dimensions of pore 140a can be accurately controlled.

Exemplary device 100 may take many forms, for example, device 100 includes a graphene layer 140 that is approximately 1-5 nm in thickness, suspended over a 1 μm wide diameter hole 140A in a 40 nm thick silicon nitride (SiN) membrane 182. In embodiments, SiN membrane 182 is suspended over an approximately 50×50 μm² aperture in a semiconductor layer coated with a 5 μm thick layer of SiO2. This exemplary device 100 may be inserted into a portable biometric detection device (not shown) that includes circuitry 110A for applying and sensing voltages (e.g., $V_B$) and currents (e.g., $i_B$) through electrodes 150A and 620. These sensed currents or voltages may be used by circuitry 110A to create a nanopore, e.g. nanopore 140, as described herein or to drive a biomolecule through hole 140A, or to sense variations in $V_B$ or $i_B$ as a biomolecule passes through hole 140A that may interpreted by circuitry 110A formed in semiconductor layer 110 to allow biomolecule detection. Circuitry 110A may be formed within device 110 and suitably coupled to electrodes 150A, 620.

In the example of FIG. 2A, the first circuit 200 includes a voltage generator 210, a driving module 220, a pore-forming module 230, and a switch 240 controlled by a control signal CS1. The voltage generator 210 is connected to the electrode layer 620 (which is in contact with chemical solution in the second chamber 130B). Voltage generator 210 may be responsive to input signal IN1 originating in control circuitry 110A. As one of skill will appreciate voltage generator 210 is configured to receive input control signal (IN1) which controls the generation of generate a reference voltage (Vref1). Vref1 may be a constant voltage, e.g., ground, VDD, or any suitable reference voltage. Vref1 may be applied to the electrode layer 620. Signal IN1 and reference voltage Vref1 may be provided by any suitable semiconductor structure within the circuit layer 110. The particulars of creating a reference voltage based on an input signal are known in the art and need not further be discussed.

Signal IN1 may alternatively be a control signal from external control circuitry; e.g., control circuitry in a biological characteristic-identifying device coupled to device 100. IN1 may be an enable signal, or characteristics of IN1 may dictate characteristics of the reference voltage (Vref1), for example Vref1=A*IN1, where A is a scalar factor such that IN1 may dictate the magnitude Vref1 in a linear fashion. It will be appreciated that IN1 may control the magnitude and duration of Vref in any suitable fashion. For example, IN1 may be a digital word that encodes a magnitude (e.g. 40 mV) with a duration (e.g. 10 ns). IN1 may be an enable signal that enables a predetermined Vref (e.g. 50 mV), or IN1 may have dynamic qualities that determine the characteristics of Vref, for example IN1 may vary dynamically according to a customized encoding as desired by the design consideration of a device 100. For example IN1 may vary between two voltages in a first power domain (e.g. 0 v-5 v), such that the variation in IN1 voltage correspond to voltage changes in Vref in a second power domain (−100 mV–100 mV) as the system requires based on design considerations that are beyond the scope of this disclosure. In other embodiments IN1 may be an external reference, e.g. VDD or ground or 0V, in which case Vref may likewise be VDD, or ground, or 0V from an external reference. Control signal IN1 may also be a current domain signal, such that Vref varies in response to variations in current supplied by IN1. In embodiments, the driving module 220, may be programmed to respond to any of Idrv, Ipore, Vbias1 or Vbias2 by controlling Vref using IN1. For example, $V_{ref}$ may be established to ensure, in coordination with other bias voltages, a particular direction of DC flow, e.g. a DC current flow from electrode 150A to electrode 620, or visa versa. Control circuitry may react to voltage variations in semiconductor device 100 to ensure that the direction of DC flow does not change, thereby ensuring that biomolecules flow in a particular direction through a nanopore 140A. Thus, in the context of this disclosure, IN1 may control the reference voltage Vref as needs dictate based on design considerations that are beyond the scope of this disclosure and according to well-known principles that need not be discussed further.

The driving module 220 is selectively connected to the electrode layer 150A and is configured to generate a bias voltage ($V_{bias1}$) applied to the electrode layer 150A. The reference voltage ($V_{ref1}$) at the electrode layer 620 and the bias voltage ($V_{bias1}$) at the electrode layer 150a result in a drive voltage across the electrode layers 620, 150A for driving a biomolecule through the pore 140A. The driving module 220 is further configured to detect a drive current ($I_{drv}$) through the electrode layers 620, 150A that is associated with the drive voltage and a corresponding resistance of the nanopore layer 140. One or more of the characteristics of the biomolecule may be determined using the drive currents ($I_{drv}$) detected by the driving module 220. As explained above, as a biomolecule passes through nanopore 140, the RC characteristics of the nanopore vary with the molecule currently passing through the nanopore 140, thereby causing known, deterministic, variations in $I_{drv}$ that may be simultaneously sensed by circuitry coupled to electrodes 150A, 620. In this way the sequence of molecules in a biomolecule may be resolved.

The pore-forming module 230 is selectively connected to the electrode layer 150A, e.g. using switch 240 and controlled by control signal CS1, and is a voltage generator configured to generate pore-forming pulses ($V_{pulse}$) applied to the electrode layer 150a for forming the pore 140a. For example, pore-forming module 230 may receive a reference voltage from voltage generator 210 and amplify the reference voltage using known principles to generate a pore forming voltage ($V_{pulse}$).

The driving module 220 is further configured to generate a bias voltage ($V_{bias2}$) applied to the electrode layer 150A. Reference voltage ($V_{ref1}$) at the electrode layer 620 and the bias voltage ($V_{bias2}$) at the electrode layer 150A together result in a pore voltage applied between electrode layers 620, 150a. Driving module 220 is further configured to detect a pore current ($I_{pore1}$) through electrode layers 620, 150A. Ipore1 is associated with the pore voltage and a corresponding resistance of the nanopore 140A, which varies in a deterministic manner as the diameter of nanopore 140A increases. A diameter/width of the pore 140A may be estimated using the pore currents ($I_{pore1}$) detected by the driving module 220. Before a pore only very small leakage currents may pass through the dielectric membrane, e.g. graphene. Thus, when a pore 140A is formed an increased flow of current $i_B$ from a first chamber, e.g. 130A, into a second chamber, e.g. 130B, through the nanopore is detected. An increase in diameter of the pore can be detected as a decrease in resistance of (or an increase in the current through) the nanopore as illustrated below.

The switch 240 is connected to the driving module 220, the pore-forming module 230, and the electrode layer 150a. Switch 240 is configured to receive a control signal (CS1) and to selectably connect either the driving module 220 or the pore-forming module 230 to electrode layer 150a. CS1 may be generated in semiconductor circuits formed in layer 110, or may be received from an external control circuit in an attached biomolecule sensing/characterization device.

Figure 2B:
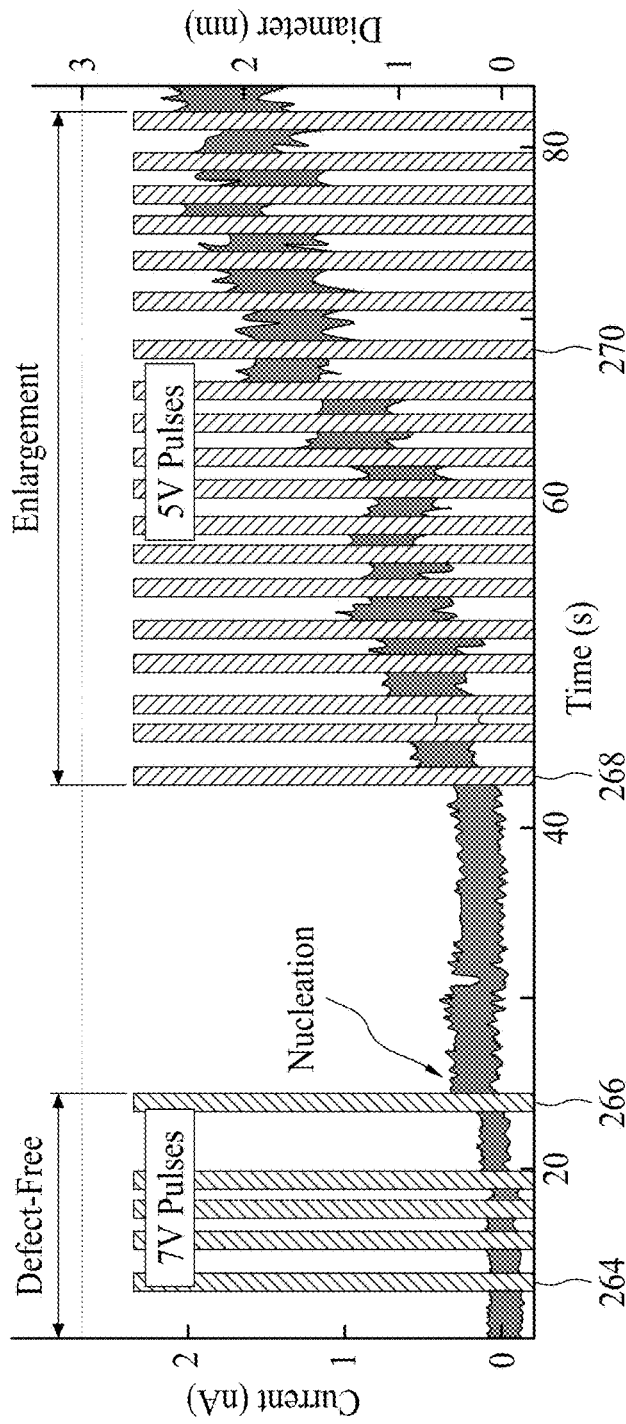
FIG. 2B illustrates current response to pulse formation of a nano-pore in accordance with some embodiments.

FIG. 2B illustrates nanopore $V_{pulse}$ during formation in a single layer of graphene, e.g. in layer 140, according to various embodiments. The single layer of graphene 140A sits atop an aperture 142A in semiconductor and insulator layers 110, 182 between a first chamber 130A and a second chamber 130B and separates two ionic solutions in each respective first and second chambers 130A, 130B. A first electrode 150A is in the first chamber 130A, and a second electrode 620 is in the second chamber 130B. Electrically connected between the first electrode 150A and the second electrode 620 is a circuit formed in a semiconductor circuit layer 110 allowing for both the measurement of current and for driving pulse formation, e.g. first circuit 200. As shown in FIG. 2B, before a nanopore (or defect in the graphene layer) is formed in graphene layer 140, circuit 200 may be configured to apply Vpulse as a series of electrical pulses 264 of a first voltage across the first electrode 150A and the second electrode 620. The first voltage may be any suitable voltage for inducing nucleation in a selected nanopore layer (here, e.g., made of a single layer of graphene, but in other embodiments made of any desirable 2D transistor). For example, in the embodiments depicted, the first voltage may be about 7 v.

Between pulses, circuit 200 is configured to sense a current flowing between the first electrode 150A and the second electrode 620. As shown, prior to nucleation of the graphene layer, e.g. 140, at time 266, at approximately twenty-seconds of $V_{pulse}$ pulses, current is approximately zero indicating that little or no current flows between first electrode 150A and second electrode 620. After time 266, when nucleation of the graphene layer occurs, forming a nanopore, current begins to flow through aperture 140A, 142A from first electrode 150A to second electrode 620. In the exemplary embodiments depicted, beginning at about a time 268 equal to 42 s, $V_{pulse}$ includes a second series of electrical pulses 270 of a second voltage, here lower than the first voltage pulses 264, are applied causing the defect, or nanopore, to increase in diameter over a period of approximately 40 seconds from about a diameter of 0.1 nm to a diameter of about 2.2 nm. This lengthier series of second pulses 270 of a lower voltage may be referred to as a voltage soaking. The second voltage may be any suitable voltage for enlarging a nanopore in a desired nanopore layer, for example in the embodiments depicted with a nanopore layer formed from a single layer of graphene, the second voltage may be about 5 v. Additionally, the relative periods of time the first voltage pulses 264 and the second voltage pulses 270 are applied may be any suitable periods to achieve the desired purposes, and are not limited to the exemplary values of 7 v and 5 v. The relationship between current and pore diameter for a given nanopore layer may be obtained by direct measurement.

FIGS. 3A-3C depict example supporting circuitry for the first circuit 200. FIG. 3A is schematic diagram illustrating an exemplary driving module 220 in accordance with some embodiments. These circuitry are provided by way of example and other suitable circuitry are within the scope of the present disclosure. The driving module 220 includes a current-to-voltage converter (IVC) 310 and an analog-to-digital converter (ADC) 320. In this way circuitry 220 formed in semiconductor device layer 110 senses the analog value changes in $i_B$, and converts the current signal (Idrv/Ipore1) signal first to a voltage then to a digital signal for transmission offchip to an external device. By converting the signal to digital in situ, noise and distortion introduced by transmitting analog signals off chip are avoided entirely. IVC 310 is configured to generate the bias voltage ($V_{bias1}$), to detect the drive current ($I_{drv}$), and to convert the drive current ($I_{drv}$) to a drive voltage ($V_{drv}$). The ADC 320 is connected to the IVC 310 and is configured to convert the drive voltage ($V_{drv}$), which is in an analog format, into a digital format so that the detected signal may be transmitted to the output 198 thereby to an external device in a digital format without concern of introduced noise and distortion masking small changes in an analog signal. One or more characteristics of the biomolecule may then be determined using the digitized drive voltages ($V_{drv}$) provided by the ADC 320.

The IVC 310 is further configured to generate the bias voltage ($V_{bias2}$), to detect the pore current ($I_{pore1}$), and to convert the pore current ($I_{pore1}$) to a pore voltage ($V_{pore1}$). The ADC 320 is further configured to convert the pore voltage ($V_{pore1}$), which is in an analog format, into a digital format. A diameter/width of the pore 140A may be estimated using the digitized pore voltages ($V_{pore1}$) provided by the ADC 320. As illustrated in FIG. 2B, nanopore diameter for a given nanopore layer may be measured based on a measured current through the nanopore. Because $V_{pore1}$ is derived from by IVC 310 according to a function selected by the designer, measuring $V_{pore1}$ similarly provides a measurement of the nanopore. While in embodiments the nanopore diameter may be measured by directly measuring the current through the nanopore, in other embodiments it is advantageous to first convert the current to be measured to a voltage and measurement taken of the converted voltage as an alternative to measuring the current directly.

In an alternative embodiment, the driving module 220 further includes an amplifier, e.g., a cascade amplifier, connected between the IVC 310 and the ADC 320 and configured to amplify the drive/pore voltages (Vdrv/Vpore1) provided by the IVC 310 prior to receipt by the ADC 320. This may be advantageous where fluctuations in pore voltages or drive currents is small, and to provide sufficient driving current where input drive currents may be too small to drive follow on sensor loads. For example, an amplifier configured in voltage follower may provide a gain of 1, such that an input voltage is equal to an output voltage, while output current is increased substantially to support follow on sensor load. It will be appreciated that any suitable amplifier may be chosen to amplify the drive/pore voltage as necessary.

FIG. 3B is a schematic diagram illustrating an exemplary IVC 310 in accordance with some embodiments. In the example of FIG. 3B, the IVC 310 includes a transimpedance amplifier 330 and a voltage generator 340. The transimpedance amplifier 330 includes an operational amplifier (op-amp) 330, a feedback resistor (Rf) 332 connected between a first input terminal 330a and an output terminal 330c of the operational amplifier (op-amp), and a feedback capacitor (Cf) 334 connected in parallel to the feedback resistor (Rf) 332.

The voltage generator 340 is connected to a second input terminal 330b of the operational amplifier (op-amp) 330, is programmable in this embodiment. Voltage generator 340 is configured to receive an input signal (IN2) and to generate an input voltage (Vin) applied to the second input terminal 330b of the operational amplifier (op-amp) that corresponds to the input signal (IN2). As with IN1, IN2 may be a control signal provided according to one or more control circuits 110A in semiconductor circuit layer 110, or by an external control device. As with IN1, generating an output of Vin according to a control signal is well known in the art and is not discussed further. IN2 allows for greater controller of the IVC 310 by allowing external control circuits (not shown) to control the amplifier as dictated by a designer according to design considerations that are beyond the scope of this disclosure other than that IN2 may be employed to control Vin as desired. As with the relationship between IN1 and Vref explained above, voltage generator 340 takes IN2 which may be of a first voltage domain and outputs Vin may be of a second domain and based on control signal IN2 as required by circuit design considerations. In one exemplary control scheme, when IN2 is 1V Vin is 10 mV and when IN2 is 2V Vin is 35 mV, but one will appreciate that IN2 may control Vin in any suitable fashion. In other embodiments IN1 may be an external reference, e.g. VDD or ground or 0V, in which case Vin may likewise be VDD, or ground, or 0V from an external reference.

The transimpedance amplifier 330 is configured to provide at the first input terminal 330a thereof the bias voltage (Vbias1/Vbias2) substantially equal to the input voltage (Vin). In this way, the bias voltage may be controlled by modulation of IN2 as desired according to design considerations. The transimpedance amplifier 330 is further configured to receive the drive/pore current (Idrv/Ipore1) and to provide at the output terminal 330c thereof the second drive/pore voltage (Vdrv/Vpore1). As one of skill in the art will readily appreciate, the gain of the transimpedance amplifier 310 is established by the magnitude of the resistance of resister 332, and the capacitance of capacitor 334 may be selected as needed to provide a low pass filter in the feedback path to increase circuit stability, thereby offsetting any capacitance, e.g. $C_{pore}$, experienced by the ionic current $i_B$.

FIG. 3C is schematic diagram illustrating an exemplary pore-forming module 230 in accordance with some embodiments. The pore-forming module 230 includes a pulse generator 350 and a voltage booster 360. The pulse generator 350 is programmable in this embodiment and is configured to receive an input signal (IN3) and to generate the pore-forming pulses (Vpulse) that correspond to the input signal (IN3). IN3, like IN1 and IN2, is a control signal and is utilized to control pore formation according to known principles. Pore-forming pulses may have any suitable magnitude as explained in reference to FIG. 2B, e.g. for embodiments including a graphene nanoribbon Vpulse may varying between 7V during pore formation and 5V during pore enlargement, or according to other embodiments other suitable voltages may be employed according to design considerations. Signal IN3 may further be provided by any suitable semiconductor structure within the circuit layer 110. In embodiments, signal IN3 is supplied via a route to a voltage source implemented in CMOS structures.

As explained above, IN3 for example may be a control signal supplied by external control circuitry. IN3 may comprise a range of suitable voltages. In some embodiments IN3 may be a toggle signal that toggles between two predetermined voltages (e.g. when IN3=50 mV, Vpulse=5V and when IN3=70 mV, Vpulse=7V). Or, IN3 may have dynamic qualities that determine the characteristics of Vpulse such that as IN3 takes many voltages on demand between various voltages, IN3 causes $V_{Pulse}$ to vary on demand as well in a like manner according to a linear function (e.g. Vpulse=A*IN3). For example, IN3 may vary between two or more voltages in a first power domain (e.g. 0 v-5 v), such that the variation in IN3 voltage correspond to voltage changes in Vref in a second power domain (0-100 mV).

Control signal IN3 may also be a current domain signal, such that Vref varies in response to variations in current supplied by IN3. This pulse generator 350 may be programmed to control Vref in response to IN3 according any suitable function. The pore-forming pulses (Vpulse) may alternate between the reference voltage (Vref1) level and a voltage level higher than the reference voltage (Vref1) level. This variation may be controlled via control signal IN3 as discussed above. The voltage booster 360 is connected to the pulse generator 330 and is configured to step up a level of the pore-forming pulses (Vpulse). Voltage booster may increase Vpulse by a predetermined factor, e.g. a factor of ten). In this way, Vpulse is within the range of voltages that will cause an enlarge nanopore formation. It will be appreciated that the voltages discussed above are by way of example only, and in particular embodiments will be dictated by design considerations and materials.

As explained in detail in reference to FIG. 2B, in one example, higher voltages are first employed in a series of pulses to cause dielectric break down, then lower voltage pulses are employed to increase pore size over a period of time, such that the longer low voltage pulses are employed the larger the diameter of the nanopore. In an embodiment, nanopores are formed in a graphene membrane using electrical pulse fabrication, as described in reference to FIG. 2B. A transmembrane current is measured to monitor pore size. A series of 250 ns 7 v electrical pulses are applied across the graphene membrane to nucleate the pore. In an embodiment, 7 v pulses are applied for approximately 25 sec at which point an appreciable increase in transmembrane current (e.g. from 0 nA to 0.2 nA) may be observed. Then, a series of low voltage 5V electrical pulses are applied to increase the diameter of the pore. This low voltage soaking signal, in an embodiment, applied over the course of 40 seconds, with 1 second interval pauses for measurement of the transmembrane current, causes the diameter of the pore to increase from approximately 0.2 nm to 2.3 nm in nearly linear fashion (e.g. by observing an increase in transmembrane current from 0.2 nA to approximately 1.8 nA). It will be appreciated that the voltages and times discussed above are by way of example only, and in particular embodiments will be dictated by design considerations and materials. The structures and circuitry depicted in FIG. 2A-2B are not intended to be limiting and in embodiments further include additional circuit components configured to sense biomolecule characteristics as the biomolecule passes through the pore 140A.

Figure 4:
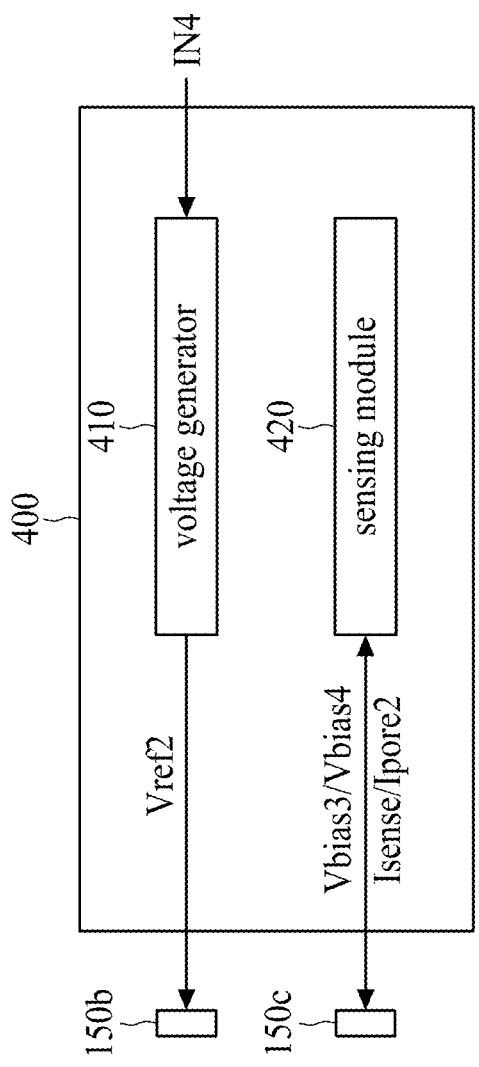
FIG. 4 is a functional block diagram illustrating an exemplary second circuit connected to electrode layers in accordance with some embodiments.

FIG. 4 is a functional block diagram illustrating an exemplary second circuit 400 formed in semiconductor layer 110. Second circuit 400 is formed for controlling a voltage applied across a nanopore layer (e.g. between terminals 150B, 150C). Second circuit may sense a transistor current $i_T$ passing through a nanopore layer (i.e. a current comprising currents such as Isense or Ipore2 that pass between 'source/drain' regions of a 2D transistors connected to the electrode layers 150B, 150C) in accordance with some embodiments. The second circuit 400 is configured to apply a sense voltage across the electrode layers 150B, 150C. And second circuit 400 is configured to detect a sense current through the electrode layers 150B, 150C that is associated with the sense voltage. As a biomolecule is driven through the pore 140a, RC characteristics of the nanopore layer 140 between electrodes 150B, 150C change in a predicable manner associated with individual sensed portions of a biomolecule (e.g., nucleotides). As the RC characteristics of the nanopore layer change, such changes affect a sensed current, e.g. variations in $I_{sense}$. Thus, alternatively to sensing drive currents passing through a nanopore, the sense currents detected by the second circuit 400 may be used to determine one or more characteristics of the biomolecule. It will be appreciated that all values of currents, voltages, and sizes are exemplary and according to various embodiments, but in other embodiments these values will take any suitable value depending on design considerations.

The second circuit 400 can also be configured to detect the diameter of the pore 140A in conjunction with (e.g., as a corroborating activity), or in the alternative to, the first circuit 200 detecting the diameter. First circuit and second circuits are each respectively configured to detect orthogonal currents $i_B$, $i_T$ passing through nanopore layer 140. Each current may differ from the other, while also being deterministically affected by changes to the RC characteristics of the nanopore layer. Therefore sensing $i_T$ and $i_B$ variations may complement each respective sensing. That is, instead of forming and detecting a size of a nanopore using ionic currents passing through the nanopore and sensed, e.g., by an electrode 150A or 620, a nanopore size may be monitored using currents created and monitored by second circuit 400, e.g. $I_{pore2}$. Or, both an ionic current $i_B$ and a transistor current $i_T$ may be used in forming and sizing a nanopore (e.g. an ionic current, e.g. $I_{pore1}$, may form the nanopore while the size of the nanopore is monitored using transistor currents like $I_{pore2}$).

In any such case, second circuit 400 may be configured apply a sensing voltage across the electrode layers 150b, 150c, and also to detect a pore current, Ipore2, through the electrode layers 150b, 150c, where Ipore2 is associated with the sensing voltage and a corresponding resistance of the nanopore layer 140, that changes as a nanopore is enlarged. Thus, aside from the pore currents detected by the first circuit 200, the pore currents detected by the second circuit 400 may alternatively be used to estimate a diameter/width of the pore 140a. When the nanopore layer, e.g. 140, is electrically conductive, instead of sensing and measuring a current passing through the chemical solution, and through the nanopore itself as with first circuit 200, alternatively, electrodes 150b and 150c may be coupled to the nanopore layer, e.g. 140, 250, and a current/voltage relationship across the nanopore layer, e.g. 140, 250, may be measured to determine nanopore diameter. For any given configuration, and selection of nanopore layer, the IV relationship across a conductive nanopore layer as a nanopore is formed, or enlarged, may be obtained by prior direct measurement in order to calibrate the sensor system.

The is a functional block diagram of FIG. 4 illustrates an exemplary second circuit 400 connected to the electrode layers 150b, 150c in accordance with some embodiments. The second circuit 400 includes a voltage generator 410 and a sensing module 420. The voltage generator 410 is connected to the electrode layer 150b, is programmable in this embodiment, and is configured to receive an input signal (IN4) as a control signal to generate a reference voltage ($V_{ref2}$) applied to the electrode layer 150b that corresponds to an input control signal (IN4) supplied, e.g. by an external control device or circuit. Signal IN4 and reference voltage Vref2 may be provided by any suitable semiconductor structure within the circuit layer 110. In embodiments, signal IN4 is supplied via a route to a voltage source implemented in CMOS structures. The particular mechanisms for controlling a voltage generator for generating a desired reference voltage using a control signal IN4 are known in the art, as discussed above, and need not further be discussed.

IN4 for example may be a control signal supplied by external control circuitry. IN4 may be a toggle signal that toggles between two predetermined Vref2 (e.g. IN4 may toggle between 50 mV and 70 mV), or IN4 may have dynamic qualities that determine the characteristics of $V_{ref2}$. For example IN4 may vary between two voltages in a first power domain (e.g. 0 v-5 v), such that the variation in IN4 voltage correspond to voltage changes in Vref2 in a second power domain (−100 mV-100 mV). In other embodiments IN4, as with IN1, IN2, may be an external reference, e.g. VDD or ground or 0V, in which case $V_{ref2}$ may likewise be VDD, or ground, or 0V. Control signal IN4 may also be a current domain signal, such that Vref2 varies in response to variations in current supplied by IN4. This voltage generator 410 may be programmed to control Vref2 in response to IN4 according to a function, which may be a linear function, or any suitable control function, e.g. $V_{ref2}=A*IN4$, where A is a scalar. Like pulse generator 230, voltage generator 410 may be programmable to employ a voltage booster configured to step up a level of the of Vref2. Voltage booster may increase $V_{ref2}$ by a predetermined factor, e.g. a factor of ten. It will be appreciated that the voltages discussed above are by way of example only, and in particular embodiments will be dictated by design considerations and materials. In embodiments, the sensing module 420 is connected to the electrode layer 150c and is configured to generate a bias voltage (Vbias3) applied to the electrode layer 150c, as a biomolecule is driven through the pore 140a. The reference voltage ($V_{ref2}$) at the electrode layer 150b and the bias voltage ($V_{bias3}$) at the electrode layer 150c result in a sense voltage ($V_{sense}$) across the electrode layers 150b, 150c which varies with the RC characteristics of the nanopore device 140. This causes proportional variation on a sensed current, e.g. $I_{sense}$ sensed by sensing module 420.

The sensing module 420 is further configured to detect a sense current ($I_{sense}$) through the electrode layers 150b, 150c that is associated with the sense voltage $V_{sense}$ and a corresponding resistance of the nanopore layer 140. One or more characteristics of the biomolecule may be determined using the sense currents ($I_{sense}$) detected by the sensing module 420.

The sensing module 420 is further configured to generate a bias voltage (Vbias4) applied to the electrode layer 150c. Voltage Vbias4 may be generated by a voltage source implemented in CMOS structures, or by any suitable means. In embodiments, sensing module 420 includes a voltage source that may generate Vbias4 as a constant voltage or sensing module 420 may, like Vref2, be programmable such that Vbias4 may be varied according any suitable function. The reference voltage (Vref2) at the electrode layer 150b and the bias voltage (Vbias4) at the electrode layer 150c result in a sense voltage across the electrode layers 150b, 150c.

The sensing module 420 is further configured to detect a pore current (Ipore2) through the electrode layers 150b, 150c that is associated with a sense voltage and a corresponding resistance of the nanopore layer 140. A diameter/width of the pore 140a may be estimated using the pore currents ($I_{pore2}$) detected by the sensing module 420.

Figure 5:
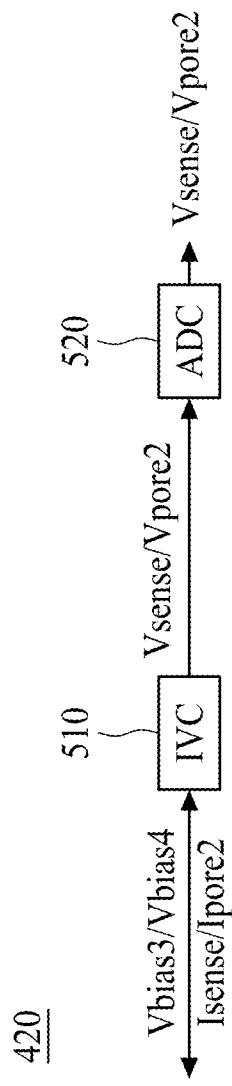
FIG. 5 is a functional block diagram illustrating an exemplary sensing module in accordance with some embodiments.

FIG. 5 is schematic diagram illustrating an exemplary sensing module 420 in accordance with some embodiments. The sensing module 420 includes a current-to-voltage converter (IVC) 510 and an analog-to-digital converter (ADC) 520. The IVC 510 and the ADC 520 may each be formed in circuit layer 110 using CMOS techniques according to any suitable semiconductor device forming process, the details of which are beyond the scope of this disclosure. The IVC 510, e.g., a transimpedance amplifier circuit, is configured to generate the bias voltage ($V_{bias3}$), to detect the sense current ($I_{sense}$), and to convert the sense current ($I_{sense}$) to a sense voltage ($V_{sense}$). In embodiments, sensing module 420 includes a voltage source creating a constant $V_{bias3}$ voltage having an associated current $I_{sense}$ that varies with the resistance between electrodes 150B and 150C. As the resistance changes responsive to a passing biomolecule, current $I_{sense}$ varies corresponding in the change in resistance caused by the biomolecules passing through nanopore 140A. The ADC 520 is connected to the IVC 510 and is configured to convert the sense voltage ($V_{sense}$), which is in an analog format, into a digital format for transmission to an external biomolecule characterization device. By converting to a digital format in situ, within semiconductor layer 110, the distance between biomolecule sensor, e.g. nanopore layer 140, and sensing circuitry is minimized thereby minimizing noise and distortion interfering with the sensed analog signal. One or more characteristic of the biomolecule may be determined using the sense voltages (Vsense) provided by the ADC 520.

During pore-formation, the IVC 510 is further configured to generate the bias voltage ($V_{bias4}$). $V_{bias}$ 4 may be a constant voltage having an associated current $I_{pore2}$ that varies with the size of the pore. While $V_{bias}$ is applied, IVC 510 is configured to detect the pore current ($I_{pore2}$) and to convert the pore current ($I_{pore2}$) voltage ($V_{pore2}$) which differs in relation to the size of the pore 140A. The ADC 520 is further configured to convert the pore voltage ($V_{pore2}$), which is in an analog format, into a digital format. A diameter/width of the pore 140A may be estimated using the pore voltages ($V_{pore2}$) provided by the ADC 520. In embodiments $V_{bias4}$ is the same as $V_{bias3}$, but as will be appreciated $V_{bias3}$ and $V_{bias4}$ may be tailored to a particular application. In embodiments, $V_{bias3}$ is generated during sensing of a biomolecule's characteristics by sensing $I_{sense}$, and $V_{bias4}$ is generated during pore formation to characterize pore size by sensing $I_{pore}$.

In an alternative embodiment, the sensing module 420 further includes an amplifier, e.g., a cascade amplifier, connected between the IVC 510 and the ADC 520 and configured to amplify the sense/pore voltages ($V_{Sense}/V_{pore2}$) provided by the IVC 510 prior to receipt by the ADC 520.

In various embodiments the signals created and sensed by first circuit 200 and second circuit 400 may be independently sensed and transmitted off chip to an external biomolecule characterization device for analysis of the sensed signals in order to characterize the sensed biomolecule or in feedback to one or more control signals or functions (e.g. CS1, IN1, IN2, IN3, IN4). In embodiments these sense signals may be analyzed singularly, or an analysis may rely on multiple sensed signals, (e.g., $i_{pore1}$, $i_{pore2}$, $i_B$, $i_T$, $i_{drv}$, $i_{sense}$), or an analysis may rely on differences between two signals (e.g., A*iporel−B*ipore2), or an analysis may rely on any suitable function of the sensed signals.

Figure 6:
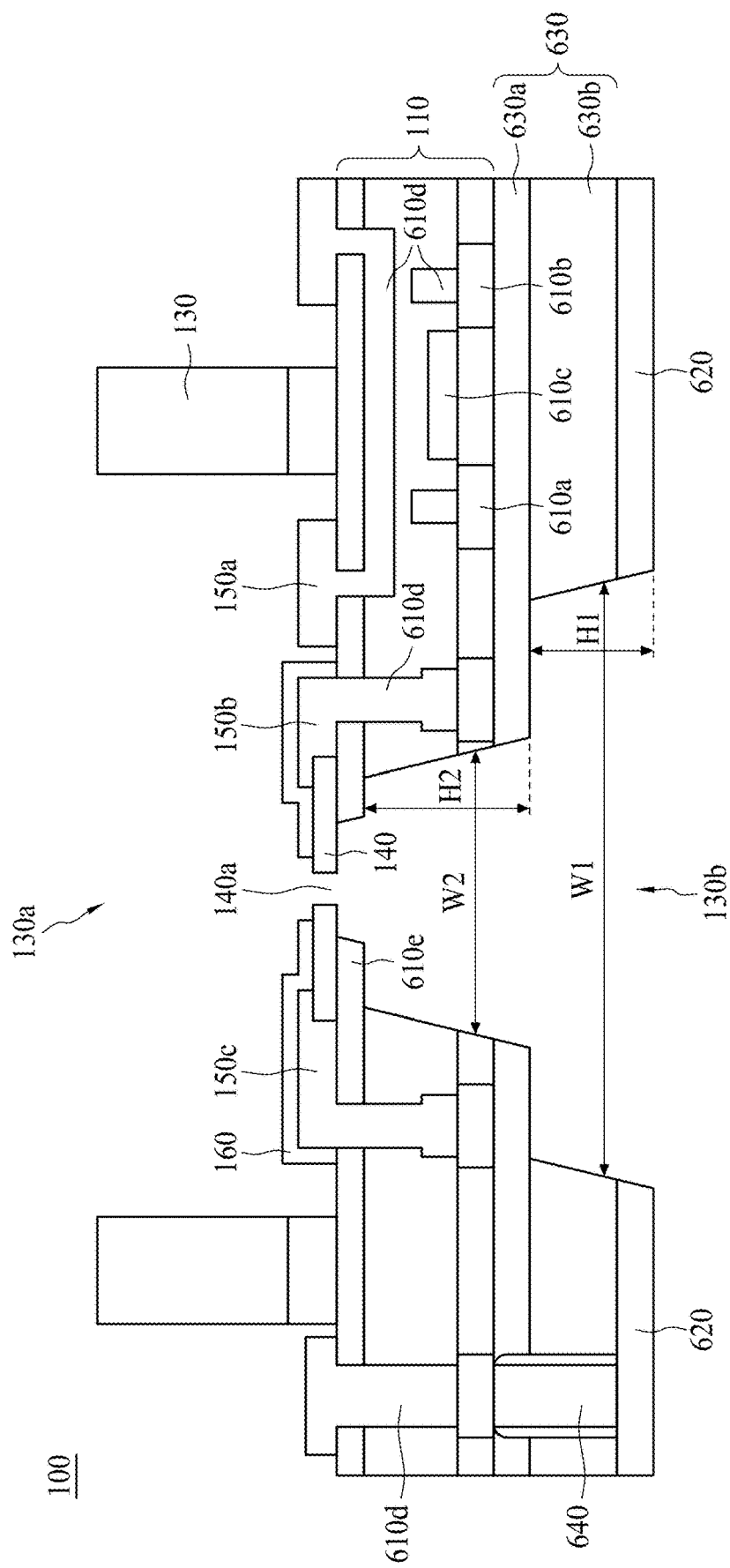
FIG. 6 is a cross sectional view illustrating an exemplary semiconductor device with integrated nanopore layer in accordance with some embodiments.

FIG. 6 is an alternate cross-sectional view illustrating aspects of an exemplary semiconductor device 100 in accordance with some embodiments and highlighting aspects of circuit layer 110 and wafer 630. As in exemplary embodiment described in FIG. 1B, the semiconductor device 100 includes a first chamber 130a and second chamber 130b, each configured to receive a work fluid or solution. The first chamber 130a is above the second chamber 130b and is in spatial communication with the second chamber 130b through the pore 140a. As illustrated in FIG. 6, the second chamber 130b includes the electrode layer 620, a wafer 630, and the circuit layer 110. The second chamber cavity 130b extends through the electrode layer 620, the wafer 630, and the circuit layer 110.

The wafer 630 is above the electrode layer 620 and, in the example of FIG. 6, is a semiconductor-on-insulator (SOI) wafer and includes a bulk substrate 630a and a buried oxide (BOX) 630b, e.g., SiO2, above the bulk substrate 630a. In this embodiment, the bulk substrate 630a has a thickness of, e.g., about 200 um. Examples of materials for the bulk substrate 630a include, but are not limited to, Si, Ge, other suitable elementary substrate material, SiC, GaAs, GaP, InP, other suitable compound substrate material, and the like. In an alternative embodiment, the wafer 630 is a bulk wafer, a ceramic wafer, a quartz wafer, a glass wafer, or the like.

A second chamber 130b may take a variety of forms, for example, as illustrated in FIG. 6, the second chamber 130b includes a cavity that extends through the wafer 630 has a width (W1), e.g., of about 500 um, and a height (H1), e.g., of about 200 um. The second chamber cavity 130b extends through the circuit layer 110 has a width (W2), e.g., about 20 um, and a height (H2), e.g., about 5 um.

The circuit layer 110 includes the first circuit 200 and the second circuit 400, described above, that are implemented using transistors, e.g., FETs. That is, in embodiments, voltage generator 210, driving module 220 (including IVC 310 and ADC 320), pore-forming module 230, and switch 240 of first circuit 200 may be one or more semiconductor structures formed within circuit layer 110 and interconnected by one or more metal layers. Similarly, in embodiments, voltage generator 410, and sensing module 420 (including IVC 510 or ADC 520) may be one or more semiconductor structures formed within circuit layer 110 and interconnected by one or more metal interconnections 610, e.g. which may be of the same composition as interconnections 111 depicted in FIG. 1B. For simplification of illustration, FIG. 6 illustrates an exemplary FET transistor comprising source drain regions 610a, 610b, and gate 610c, but it will be appreciated that according to fabrication techniques many FETs may be formed and interconnected to create the components of first circuit 200 and second circuit 400 in circuit layer 110. For illustration, circuit layer 110 is formed with a source region 610a, a drain region 610b, and a gate structure 610c above a channel region between the source and drain regions 610a, 610b. The source and drain regions 610a, 610b and the gate structure 610c constitute an exemplary FET that may be a component structure of first circuit 200 or second circuit 400.

The circuit layer 110 further includes a plurality of exemplary interconnects, e.g., interconnect 610d, that in various embodiments connect the transistors thereof to each other, thereby realizing the first and second circuits 200 and 400 within circuit layer 110 as explained above. The interconnects 610d further connect, as with interconnections 111, the components structures forming first circuit 200 and the electrode layers 150a, 620 to each other, or interconnects connect the component structures forming second circuit and the electrode layers 150b, 150c to each other. In this way, components comprising voltage generator 210 (e.g., 310, 330, and 340) may be formed in circuit layer 110, and may supply Vref1 to second chamber 610 via interconnections, such as through substrate via (TSV) 640, to electrode 620. Similarly, driving module 220 components (such as IVC 310 and ADC 320) may be formed in circuit layer 110 and may supply and receive Vbias1/Vbias2 and Idrv/Ipore1 to first chamber 130a (through switch 240 also formed in circuit layer 110)) through interconnection like 610d, e.g. 111, to electrode 150a. Similarly, pore-forming module 230 may be formed of various semiconductor structures as described above, and may provide Vpulse to first chamber 130a via switch 240 and interconnections, e.g. 610d or 111, to electrode 150a.

In embodiments, the second circuit 400 may also be formed of various semiconductor components within circuit layer 110 and interconnected through interconnections 610d. Sensing module 420 (including component IVC 510 and ADC 520) may be formed of one or more semiconductor structures formed in circuit layer 110, and may provide Vbias3/Vbias4 and Isense/Ipore2 to pad 150c (coupled to a nanopore layer, e.g. 140, 250) via interconnections 610d. Similarly, voltage generator 410 may be formed of one or more semiconductor structures within circuit layer 110 and capable of providing Vref2 to pad 150b (also coupled to a nanopore layer, e.g. 140) via interconnections 610d. The circuit layer 110 further includes at a top surface thereof a passivation layer 610e that covers/insulates the interconnects 610d.

The second chamber 130b further includes a through substrate via (TSV) 640 that extends from circuit layer 110 to a bottom surface of the wafer 640 and that connects the first circuit 200 and the electrode layer 620 to each other.

The circuit layer 110 may further include other active components, e.g., diodes and other type of transistors such as a bipolar junction transistor (BJT), and passive components, e.g., resistors, capacitors, inductors, and the like.

FIG. 7 is a flow chart illustrating an exemplary method 700 of manufacturing a semiconductor device, e.g., semiconductor device 100, in accordance with some embodiments. In operation 710, a chamber, e.g., second chamber 610, is formed. In an embodiment, the chamber includes a circuit layer, e.g., circuit layer 110, and defines a chamber cavity, e.g., second chamber cavity 610a, that extends through the circuit layer. In operation 720, a nanopore layer, e.g., nanopore layer 140, is transferred from a source substrate to the circuit layer 110, thereby the nanopore layer may form a boundary between chamber cavities 130a, 130b where they meet, e.g. orifice 142A.

Figure 8A:
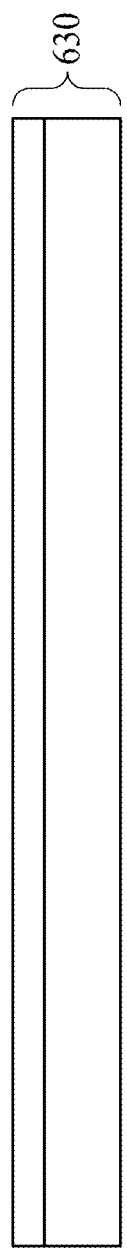
FIGS. 8A-8U are cross sectional views illustrating an exemplary semiconductor device at various stages of manufacturing in accordance with some embodiments.

FIGS. 8A-8R are sectional views of a semiconductor device, e.g., semiconductor device 100, at various stages of manufacturing in accordance with some embodiments, e.g., as produced using operations described above with reference to method 700. Method 700 will now be described with further reference to FIGS. 1, 2, 3A, 3C, 4, 5, and 8A-8R for ease of understanding. It is understood that method 700 is applicable to structures other than those of FIGS. 1, 2, 3A, 3C, 4, 5, and 8A-8R. Further, it is understood that additional operations can be provided before, during, and after method 700, and some of the operations described below can be replaced or eliminated, for other embodiments of method 700.

Figure 8B:

FIG. 8A illustrates an exemplary structure resulting after receiving/providing a wafer 630. In embodiments wafer 630 comprises an oxide layer over a SOI substrate. The oxide layer may comprise BOX. FIG. 8B illustrates an exemplary structure resulting after formation of a TSV 640 that extends from a top surface to a bottom surface of the wafer 630. The formation of the TSV 640 includes: performing a lithographic patterning and etching to form a TSV opening through the wafer 630; coating with a TSV liner, e.g., oxide, a TSV sidewall that defines the TSV opening; and filling the TSV opening with a TSV material, e.g., polysilicon.

The TSV opening is filled with the TSV material using a deposition process, such as chemical vapor deposition (CVD), atomic layer deposition (ALD), physical vapor deposition (PVD), other suitable depositing/forming/filling/growing process, derivatives thereof, or a combination thereof.

Figure 8C:
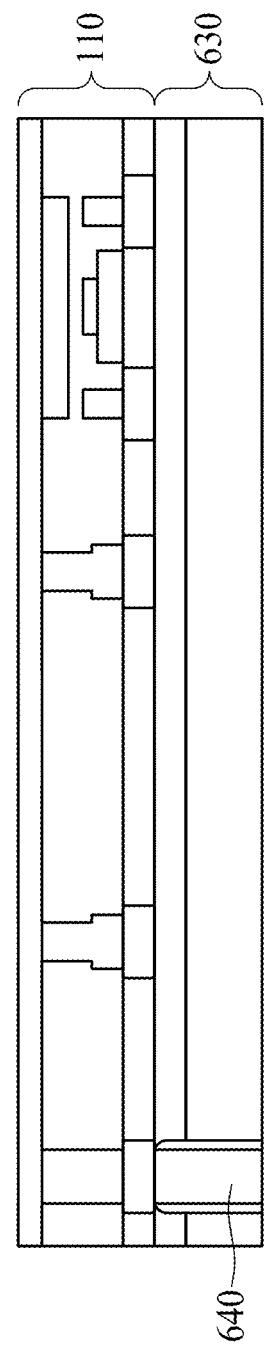

FIG. 8C illustrates an exemplary structure resulting after performance of operation 710 and depicts a circuit layer 110 above the wafer 630. The formation of the circuit layer 110 includes: depositing a semiconductor material, e.g., silicon, germanium, other suitable semiconductor material, or a combination thereof, on the top surface of the wafer 630 to form an active layer; form transistors over the active layer; depositing inter-layer dielectric (ILD) material, e.g., SiO2 or any other low-K dielectric material, on the active layer; performing lithographic patterning and etching to form openings in the ILD; filling the openings with a conductive material to form interconnects, e.g., interconnect 150d, that connect the transistors to each other, resulting in a first and second circuits, e.g., first and second circuits 200, 400, respectively; and depositing a passivation layer material, e.g., SiN, on the ILD.

Figure 8D:
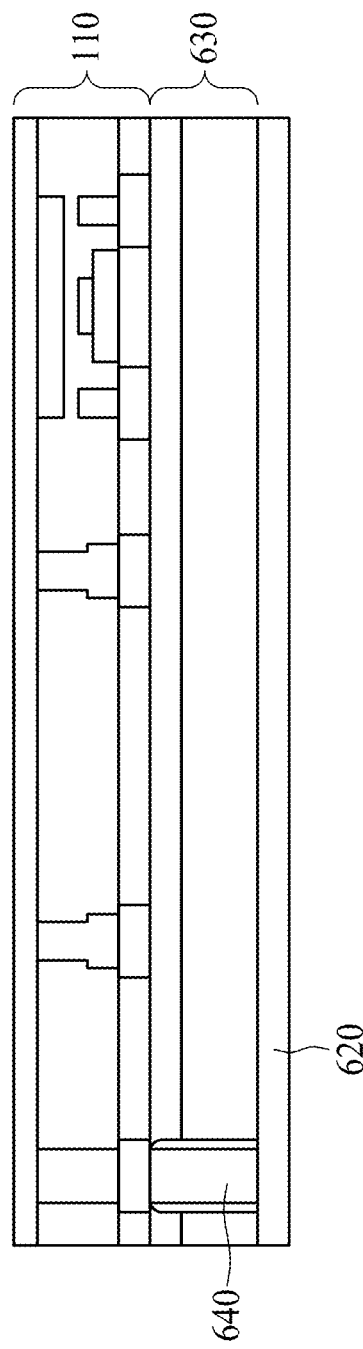
Figure 8E:
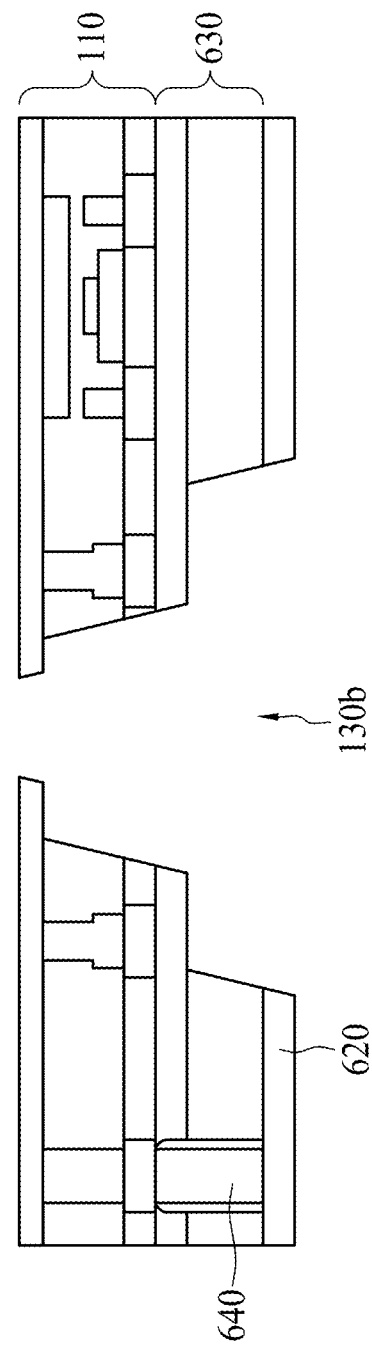

FIG. 8D illustrates an exemplary structure resulting after formation of an electrode layer 620 on the bottom surface of the wafer 630. FIG. 8E illustrates an exemplary structure resulting after formation of a chamber cavity 130b that extends through the electrode layer 620, the wafer 630, and the circuit layer 110.

Next, formation of a nanopore layer 140 is described hereinafter. FIG. 8F illustrates an exemplary structure resulting after growth of a nanopore device layer 140, on a metal catalyst 810, e.g., a copper-based metal catalyst. The growth of the nanopore layer 140 includes: receiving/providing the copper-based metal catalyst; annealing the copper-based metal catalyst at a temperature of, e.g., greater than about 800° C., to clean the copper-based metal catalyst; depositing nanopore layer 140 material on the copper-based metal catalyst, using e.g., Ar, CH4, and H2, such as by CVD at a temperature of, e.g., about 1000 degrees Celsius or plasma enhanced CVD (PECDV) at a temperature of, e.g., greater than about 450 degrees Celsius; and annealing the resulting structure at a temperature of, e.g., greater than about 600 degrees Celsius.

FIG. 8G illustrates an exemplary structure resulting after coating, e.g., spin coating, the nanopore layer 140 with a source substrate 820, e.g., a thin layer of polymer, such as poly methyl methacrylate (PMMA). The source substrate 820 protects the nanopore layer 140 from cracks during the transfer of the nanopore layer 140 to the structure of FIG. 8E, as described below.

FIG. 8H illustrates an exemplary structure resulting after removal, such as by dry or wet etching, of the copper-based metal catalyst 810 from the structure of FIG. 8G. FIG. 8I illustrates an exemplary structure resulting after sizing the nanopore layer 140 to a length of, e.g., about 200 um, and a width of, e.g., about 200 um, using e.g., lithographic, e.g., electron beam lithographic (EBL), patterning and etching.

FIG. 8J illustrates an exemplary structure resulting after performance of removing the graphene layer form source substrate 820 and then performing a transferring operation, e.g., operation 720. FIG. 8J depicts the nanopore layer 140 transferred, unformed, from the source substrate 820 to the structure of FIG. 8E. In this embodiment, the transfer operation includes removing the graphene layer from the source substrate 820 and then bonding the nanopore layer 140 to the circuit layer 110.

FIG. 8K illustrates an exemplary structure resulting after resizing the nanopore layer 140 to a shorter length, e.g., about 100 nm to about 160 nm, and a narrower width, e.g., about 80 nm, such as by lithographic, e.g., EBL, patterning and etching.

Figure 8L:
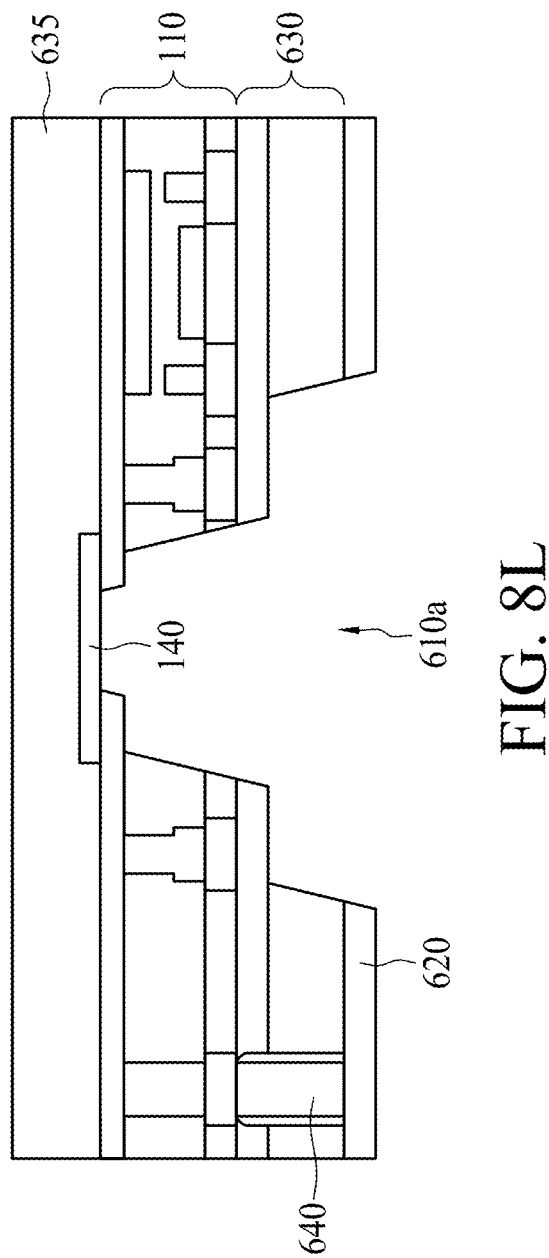
Figure 8M:
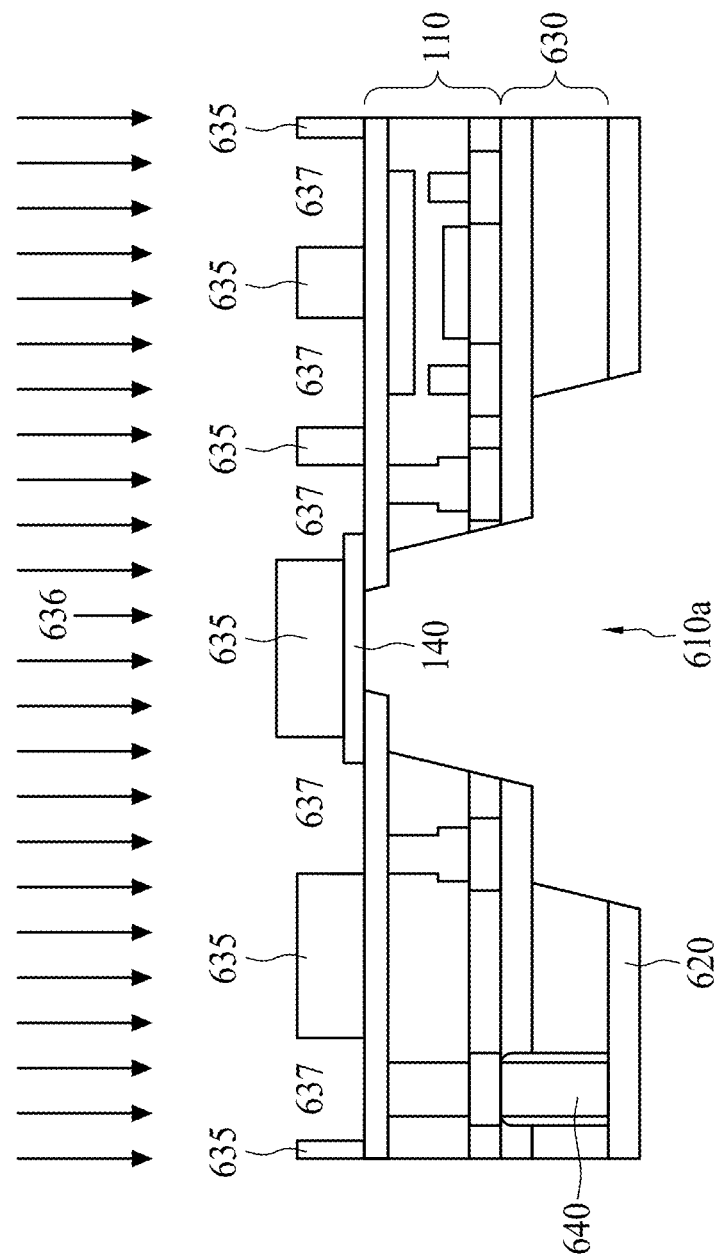
Figure 8N:
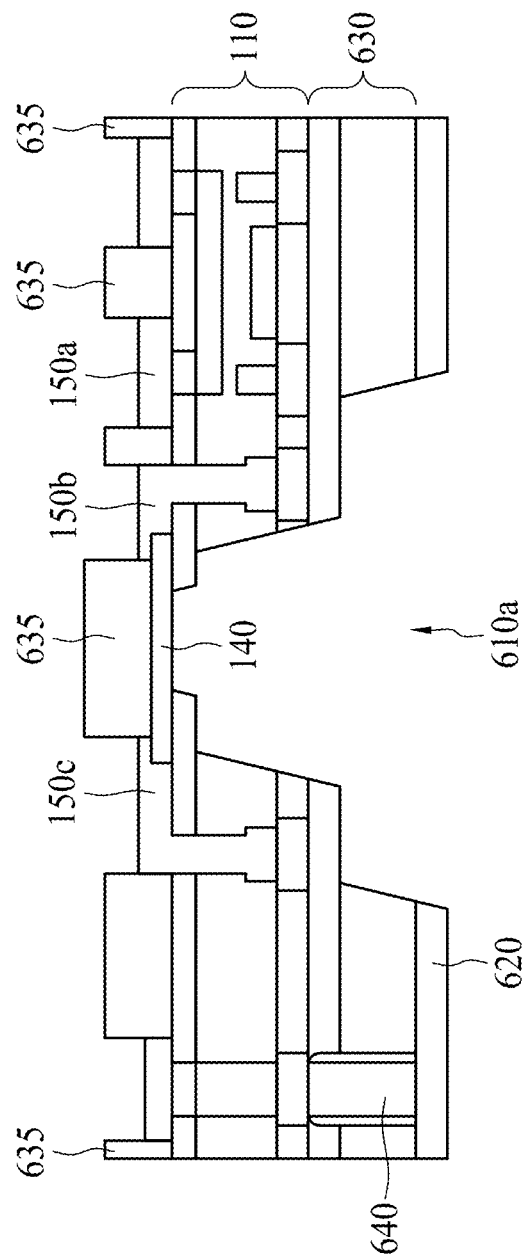
Figure 8O:
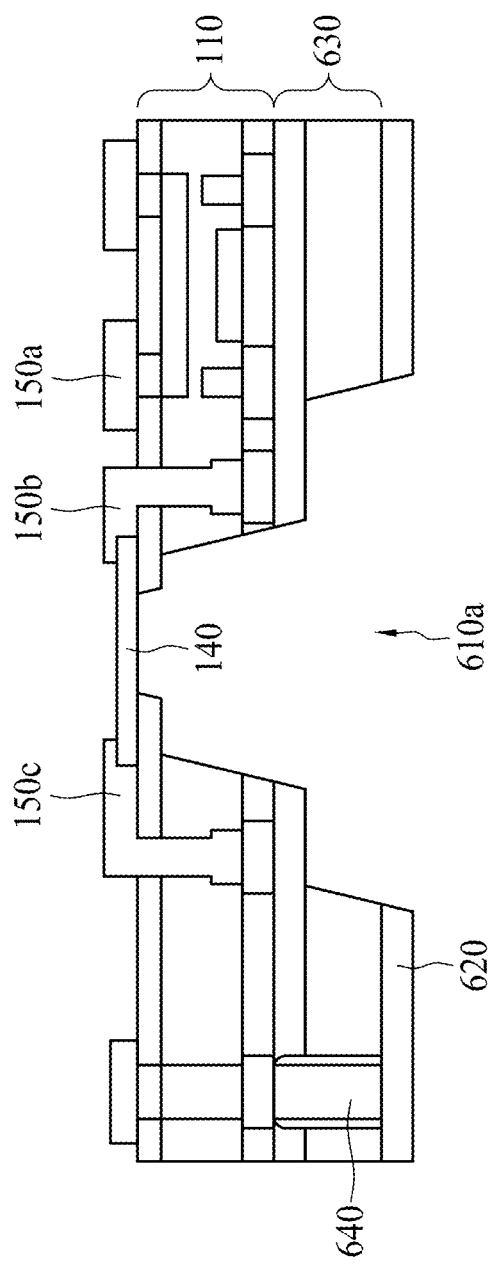
Figure 8P:
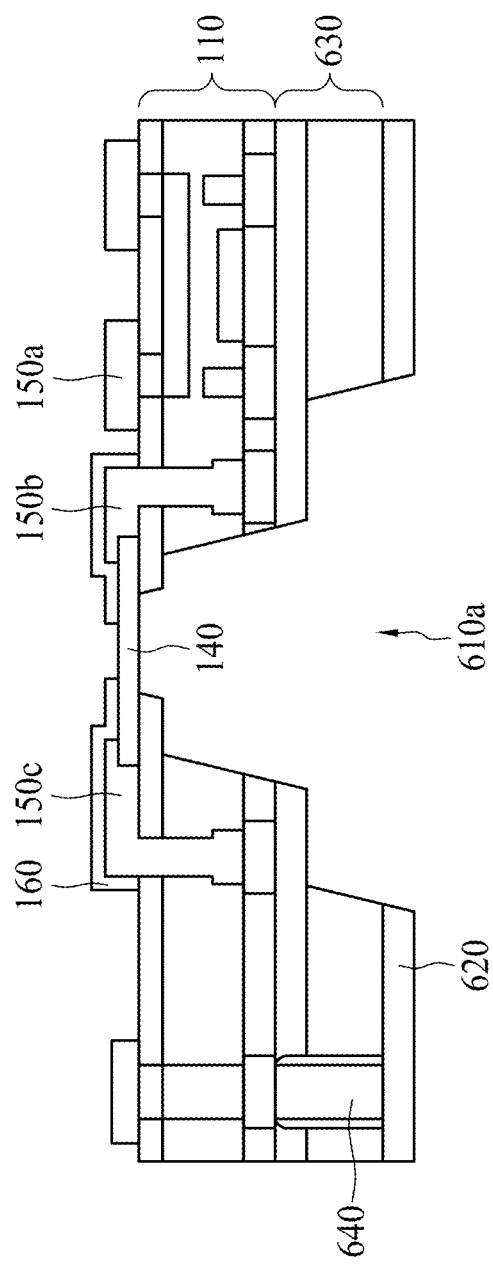

FIG. 8L illustrates growing a sacrificial layer 635 on the structure of FIG. 8K. FIG. 8M illustrates performing lithographic patterning and etching 636 to form openings 637 that extend through the sacrificial layer; and FIG. 8N illustrates the openings created in reference to FIG. 8M with conductive material e.g. 150a, 150b; subsequently, the sacrificial layer is removed as shown in FIG. 8O. FIG. 8O illustrates an exemplary structure resulting after formation of electrode layers 150a, 150b, 150c. In embodiments, the formation of the electrode layers 150a, 150b, 150c may include standard techniques for forming electrode layers over a semiconductor circuit layer. In one embodiment this includes the steps shown in FIGS. 8L-8N:

FIG. 8P illustrates an exemplary structure resulting after formation of an insulating layer 160 that covers the electrode layers 150b, 150c and first and second end portions of the nanopore layer 140. The formation of the insulating layer 160 includes: conformably depositing a material, e.g., Al2O3, over the electrode layers 150b, 150c and the nanopore layer 140; and removing the insulating layer 160 on an intermediate portion of the nanopore layer 140.

Next, formation of a chamber wall, e.g., chamber wall 130, is described hereinafter. FIG. 8Q illustrates an exemplary structure resulting after patterning a first layer 830, e.g., polymer, over a second layer 130, e.g., silicon, glass, other suitable material for a chamber wall, and the like. FIG. 8R illustrates an exemplary structure resulting after etching the second layer 130 using the first layer 830 as a mask to form a chamber cavity 130a in the second layer 130. FIG. 8S illustrates an exemplary structure resulting after bonding the second layer 130 to the structure of FIG. 8M, e.g. using the first layer 830 as an adhesive.

Next, formation of a pore 140a in the nanopore layer 140 is described hereinafter. FIG. 8T illustrates an exemplary structure resulting after filling the chamber cavities 130b, 130a with a chemical solution 800. FIG. 8U illustrates an exemplary structure resulting after formation of a pore 140a in the nanopore layer 140, e.g. by the process described above in reference to first circuit 200. The formation of a pore 140a may include: the voltage generator 210 receiving an input signal (IN1) instructing generation of a reference voltage (Vref1), e.g., about 0V, applied to the electrode layer 620 that corresponds to the input signal (IN1); the switch 240 receiving a control signal (CS1) and selectively connecting the pore-forming module 230 to the electrode layer 150a in response to the control signal (CS1); the pore-forming module 230 receiving an input signal (IN3) instructing generation of high pore-forming pulses, e.g., about 7.0 V, applied to the electrode layer 150a, thereby forming the pore 140a; subsequently the pore-forming module 230 receiving an input signal (IN3) instructing generation low pore-forming pulses, e.g., about 5.0 V, applied to the electrode layer 150a, thereby adjusting a diameter/width of the pore 140a. It will be appreciated that the voltages described above are by way of example only and in practice a suitable voltage is selected based on the solution and the nanopore layer device, e.g. 140.

In some embodiment, method 700 includes: the switch 240 receiving a control signal (CS1) and selectively connecting a driving module 220 to the electrode layer 150a in response to the control signal (CS1); the driving module 220 generating a bias voltage (Vbias2) applied to the electrode layer 150a that results in a pore voltage across the electrode layers 620, 150a; the driving module 220 detecting a pore current (Ipore1) through the electrode layers 620, 150a that is associated with the pore voltage and a corresponding resistance of the nanopore layer 140; the driving module 220 converting the pore current (Ipore1) to a pore voltage (Vpore1); and the driving module 220 converting the pore voltage (Vpore1), which is in an analog format, into a digital format. A diameter/width of the pore 140a may be estimated using the pore voltages (Vpore1).

In other embodiments, method 700 includes: the voltage generator 410 receiving an input signal (IN4) and generating a reference voltage (Vref2), e.g., about 0V, applied to the electrode layer 150b that corresponds to the input signal (IN4); The sensing module 420 generating a bias voltage (Vbias4) applied to the electrode layer 150c that results in a pore voltage across the electrode layers 150b, 150c; the sensing module 420 detecting a pore current (Ipore2) through the electrode layers 150b, 150c that is associated with the pore voltage and a corresponding resistance of the nanopore layer 140; The sensing module 420 converting the pore current (Ipore2) to a pore voltage (Vpore2); and the sensing module 420 converting the pore voltage (Vpore2), which is in an analog format, into a digital format. A diameter/width of the pore 140a may be estimated using the pore voltages (Vpore2).

Figure 9:
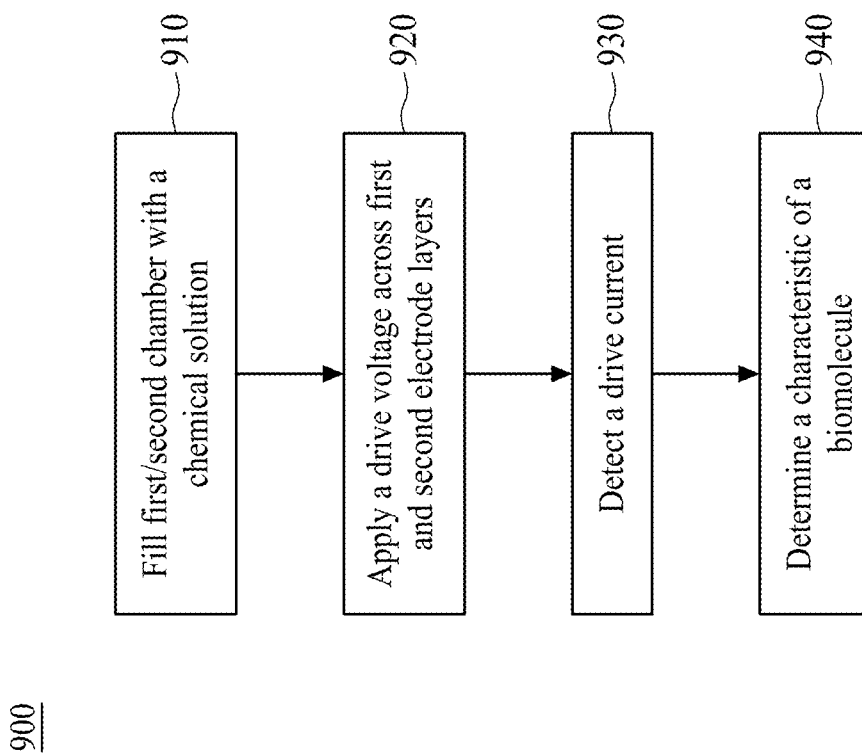
FIG. 9 is a flow chart illustrating an exemplary method of determining a biomolecule characteristic in accordance with some embodiments.

FIG. 9 is a flow chart illustrating an exemplary method 900 of determining a biomolecule characteristic in accordance with some embodiments. Method 900 will now be described with further reference to FIGS. 1A-1D, 2A, 3A-3C, 4, and 5 for ease of understanding. It is understood that method 900 is applicable to structures other than those of FIGS. 1A-1D, 2A, 3A-3C, 4, and 5. Further, it is understood that additional operations can be provided before, during, and after method 900, and some of the operations described below can be replaced or eliminated, for other embodiments of method 900.

In operation 910, the first and second chamber cavities 130a, 130b are filled with a chemical solution. Next, a biomolecule is placed in the chemical solution in the first chamber cavity 130a, or the second chamber 130b.

In operation 920, the first circuit 200 applies across the electrode layers 620, 150a a drive voltage for driving the biomolecule from the first chamber cavity 130a to the second chamber cavity 130b through the pore 140a (or visa versa). In this embodiment, operation 920 includes: the voltage generator 210 receiving an input signal (IN1) and generating a reference voltage (Vref1) applied to the electrode layer 620 that corresponds to the input signal (IN1); the switch 240 receiving a control signal (CS1) and connecting the driving module 220 and the electrode layer 150a to each other; the driving module 220 generating a bias voltage (Vbias1) applied to the electrode layer 150a that results in the drive voltage.

In operation 930, driving module 220 detects a drive current (Idrv) through the electrode layers 620, 150a that is associated with the drive voltage and a corresponding resistance of the nanopore layer 140.

In operation 940, one or more characteristics of the biomolecule are determined using the drive currents ($I_{drv}$). In this embodiment, operation 940 includes: the driving module 220, which in embodiments may be implemented in CMOS structures formed in circuit layer 110. As illustrated voltage $V_{bias1}$ is shown as applied to 150a for illustrative purposes, as it will be appreciated that the voltage is supplied via the interconnected semiconductor structures within circuit layer 110. Similarly as illustrated voltage $V_{ref1}$ is shown as applied to layer 620. $V_{ref1}$ may be generated by voltage generator 210, which is similarly implemented in circuit layer 110. By applying these voltages at their respective terminals, establishing a voltage $V_{bias}$–$V_{ref1}$ across the nanopore barrier which drives a biomolecule through the nanopore. As the biomolecule passes through the nanopore, the resistance varies along the length of the biomolecule as it passes. $V_{bias}$–$V_{ref1}$ is associated with a transmembrane current $I_{drv}$ that varies in proportion to the varying resistance caused by the passing of the biomolecule. In embodiments, $I_{drv}$ is sensed by, converting the drive current ($I_{drv}$) to a drive voltage ($V_{drv}$) with IVC 310. IVC 310 converts $I_{drv}$ to a voltage, the drive voltage ($V_{drv}$). In embodiments, the drive voltage $V_{drv}$, which in an analog format, is then converted into a digital format, which is then formatted to a biological characteristic determining device, which then determines the biomolecule characteristic based on the drive voltages ($V_{drv}$).

In an embodiment, method 900 further includes: the voltage generator 410 receiving an input signal (IN4) and generating a reference voltage ($V_{ref2}$) applied to the electrode layer 150b. And sensing module 420 generating a bias voltage ($V_{bias3}$) applied to the electrode layer 150c that results in a sense voltage across the electrode layers 150b, 150c. Sensing module 420 detects a sense current ($I_{sense}$) through the electrode layers 150b, 150c that is associated with the sense voltage and a corresponding resistance of the nanopore layer 140. In embodiments, the sensing module 420 converts the sense current ($I_{sense}$) to a sense voltage ($V_{sense}$). The sense voltage ($V_{sense}$) is then converted into a digital format, and may be forwarded to a biological characteristic sensing device, and one or more characteristics of the biomolecule may be determined using the sense voltages (Vsense).

Figure 10:
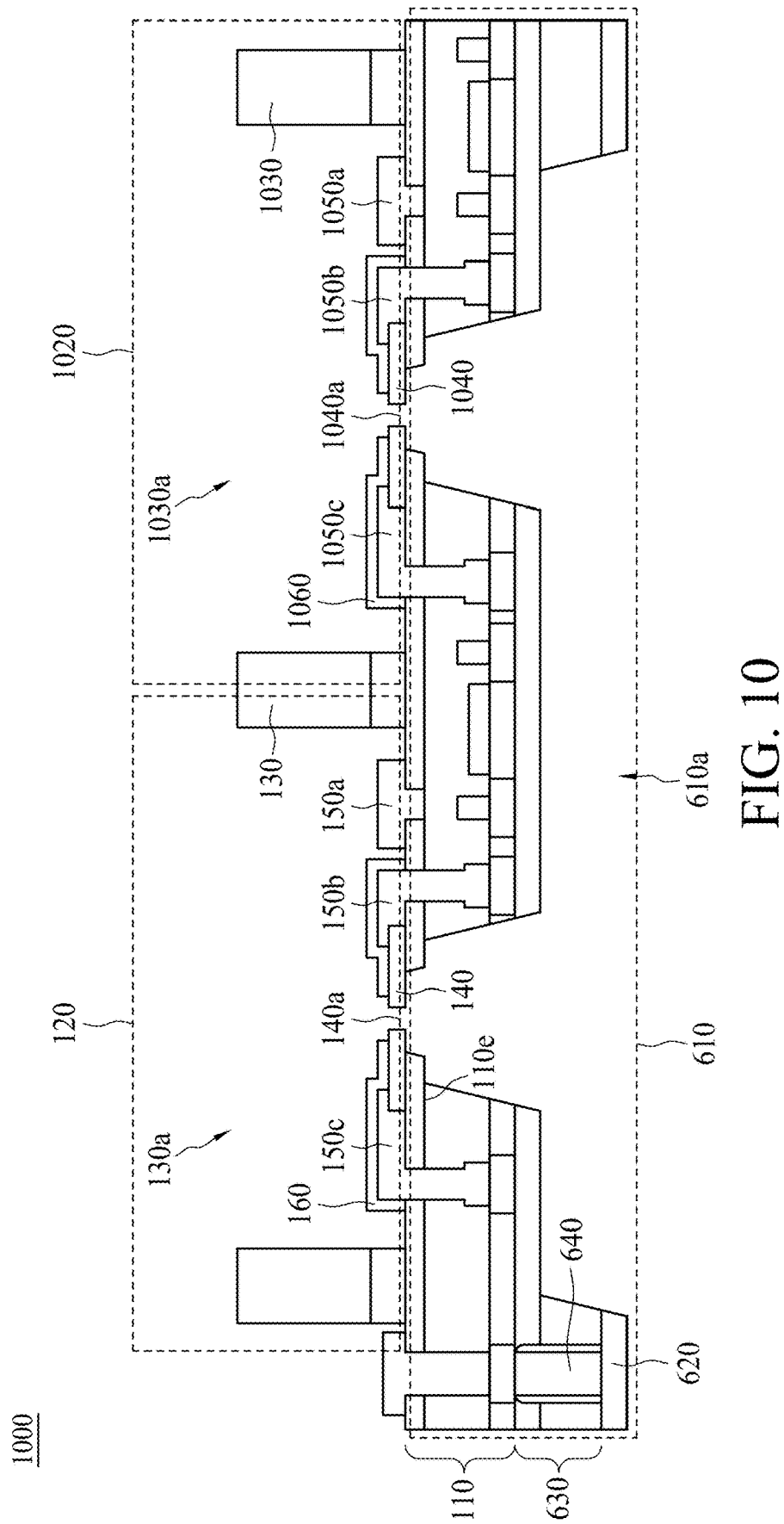
FIG. 10 is a cross sectional view illustrating an exemplary semiconductor device in accordance with some embodiments.

Although the semiconductor device 100 is exemplified using one first chamber 130a, highlighted by square 120, it should be understood that, after reading this disclosure, the number of first chambers 130a may be increased. For example, FIG. 10 is a cross sectional view illustrating an exemplary semiconductor device 1000 in accordance with some embodiments. When compared to the semiconductor device 100, the semiconductor device 1000 includes aspects of device 100 and further includes a chamber 1030a, highlighted in square 1020. The construction of the chamber 1030a is similar to that of the chamber 130a. In particular, the chamber 1030a includes a chamber wall 1030, a nanopore layer 1040, electrode layers 1050a, 1050b, 1050c, and an insulating layer 1060.

The chamber wall 1030 is formed on the circuit layer 110, such as by bonding the chamber wall 1030 to the circuit layer with the use of an adhesive. The chamber wall 1030 defines a chamber cavity 1030a therein configured to receive a chemical solution (not shown). The chamber wall 1030 may be, for example one or more silicon caps.

The nanopore layer 1040 is disposed in the chamber cavity 1030a, is formed in situ by semiconductor circuits in circuit layer 110, (e.g. a first circuit 200) and has first and second end portions and an intermediate portion between the first and second end portions and formed with a pore 1040a therethrough.

The electrode layer 1050a is disposed in the chamber cavity 1030a and is formed over the circuit layer 110. The electrode layers 1050b, 1050c are disposed in the chamber cavity 1030a, are formed over the circuit layer 110, and are connected to first and second end portions of the nanopore layer 1040, respectively. The insulating layer 1060 covers the electrode layers 1050b, 1050c and the first and second end portions of the nanopore layer 1040.

Figure 11:
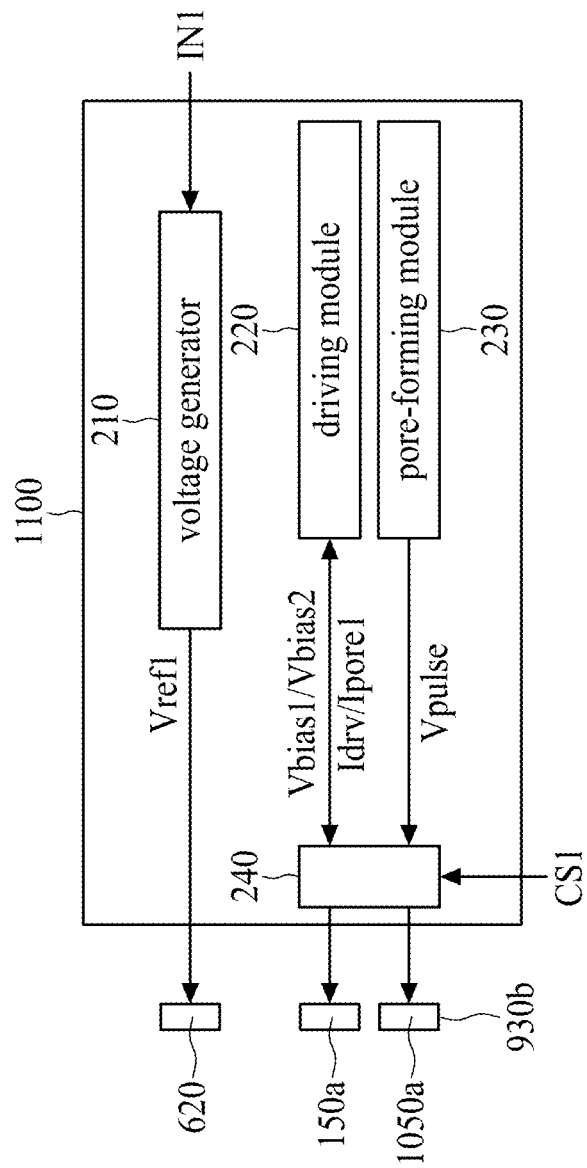
FIG. 11 is a functional block diagram illustrating an exemplary third circuit in accordance with some embodiments.
Figure 12:
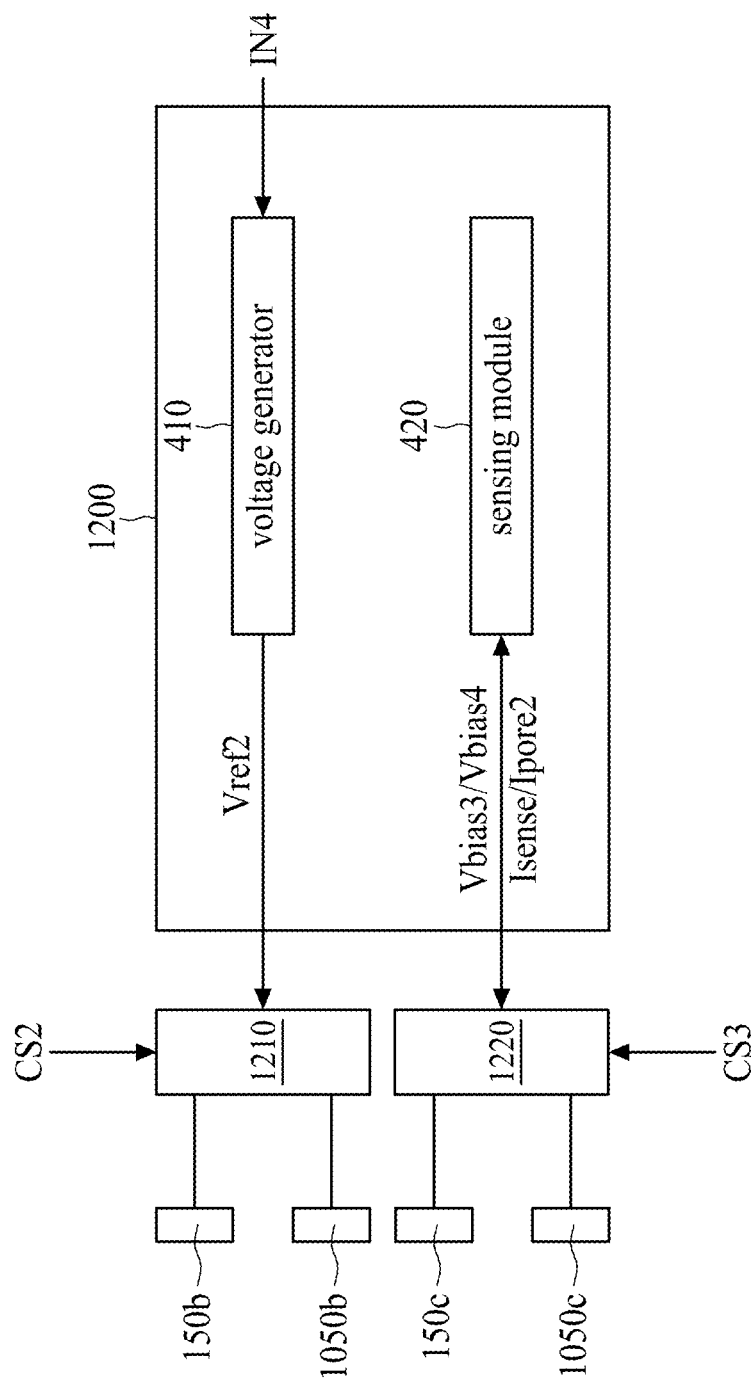
FIG. 12 is a functional block diagram illustrating an exemplary fourth circuit in accordance with some embodiments.

Further, the circuit layer 110 includes, instead of the first and second circuits 200, 400, third and fourth circuits 1100, 1200, shown in FIGS. 11 and 12, respectively. FIGS. 11 and 12 are schematic diagrams illustrating exemplary third and fourth circuits 1100, 1200, respectively, in accordance with some embodiments. When compared with the first circuit 200, the switch 240 of the third circuit 1100 comprises a driving module 220, a pore-forming module 230, and is coupled to electrode layers 150a, 1050a. A switch 240 of the third circuit 1100 is configured to receive a control signal (CS1) to selectably connect either a driving module 220 or a pore-forming module 230 to either the electrode layer 150a or the electrode layer 1050a in response to the control signal (CS1).

When compared with the second circuit 400, the fourth circuit 1200 further includes switches 1210, 1220. The switch 1210 is connected to the voltage generator 410 and the electrode layers 150b, 1050b and is configured to receive a control signal (CS2) to selectably connect a voltage generator 410 to either of an electrode layer 150b or an electrode layer 1050b in response to the control signal (CS2).

Switch 1220 is connected to the sensing module 420 and the electrode layers 150c, 1050c and is configured to receive a control signal (CS3) to selectably connect the sensing module 220 and either the electrode layer 150c or the electrode layer 1050c to each other in response to the control signal (CS3).

Figure 13:
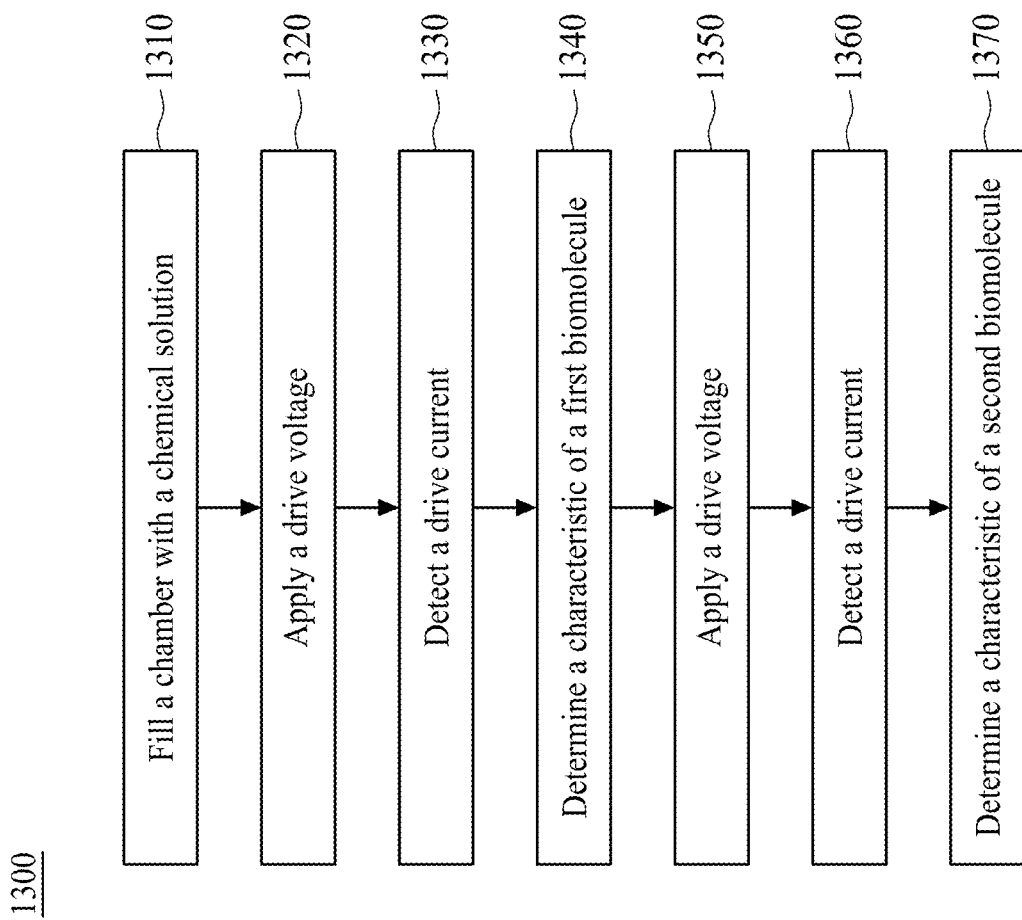
FIG. 13 is a flow chart illustrating an exemplary method of determining a biomolecule characteristic in accordance with some embodiments.

FIG. 13 is a flow chart illustrating a method 1300 of determining a biomolecule characteristic in accordance with some embodiments. Method 1300 will now be described with further reference to FIGS. 10-12 for ease of understanding. It is understood that method 1300 is applicable to structures other than those of FIGS. 10-12. Further, it is understood that additional operations can be provided before, during, and after method 1300, and some of the operations described below can be replaced or eliminated, for other embodiments of method 1300.

In operation 1310, the chamber cavities 130a, 610a, 1030a are filled with a chemical solution. Next, first and second biomolecules (not particularly illustrated, but see FIG. 14 for exemplary biomolecule 1408 suspended in solution passing through a nanopore) are placed in the chemical solution in the chamber cavities 130a, 1030a, respectively.

In operation 1320, the third circuit 1100 applies a drive voltage across the electrode layers 620, 150a for driving the first biomolecule from the chamber cavity 130a to the chamber cavity 610a through the pore 140a. In an embodiment, operation 1320 includes: the voltage generator 210 receiving an input signal (IN1) and generating a reference voltage ($V_{ref1}$) applied to the electrode layer 620 that corresponds to the input signal (IN1); the switch 240 receiving a control signal (CS1) and connecting the driving module 220 and the electrode layer 150a to each other; and the driving module 220 thereby generating a bias voltage ($V_{bias1}$) applied to the electrode layer 150a that results in the drive voltage.

In operation 1330, the driving module 220 detects a drive current (Idrv) through the electrode layers 620, 150a that is associated with the drive voltage and a corresponding resistance of the nanopore layer 140.

In operation 1340, one or more characteristics of the first biomolecule, e.g. DNA (not particularly illustrated, but see FIG. 14 for exemplary biomolecule 1408 suspended in solution passing through a nanopore), are determined from variations in drive currents ($I_{drv}$) that are responsive to a characteristics of a biomolecule passing through nanopore 140a. In an embodiment, operation 1340 includes: the driving module 220 converting the drive current (Idrv) to a drive voltage (Vdrv); the driving module 220 converting the drive voltage (Vdrv), which is in an analog format, into a digital format; and determining the first biomolecule characteristic using the drive voltage (Vdrv).

In operation 1350, the first circuit 1100 applies a drive voltage across the electrode layers 620, 1050a for driving the second biomolecule, e.g. RNA, from the chamber cavity 1030a to the chamber cavity 610a through the pore 1040a. In this embodiment, operation 1350 includes: the voltage generator 210 receiving an input signal (IN1) and generating reference voltage (Vref1) applied to the electrode layer 620 that corresponds to the input signal (IN1); the switch 240 receiving a control signal (CS1) and connecting the driving module 220 and the electrode layer 1050a to each other; and the driving module 220 generating a bias voltage (Vbias1) applied to the electrode layer 1050a that results in the drive voltage.

In operation 1360, the drive module 220 detects a drive current (Idrv) through the electrode layers 620, 1050a that is associated with the drive voltage and a corresponding resistance of the nanopore layer 1040.

In operation 1370, one or more characteristics of the second biomolecule are determined determined from variations in drive currents ($I_{drv}$) that are responsive to a characteristics of a biomolecule passing through nanopore 1040a. In this embodiment, operation 1370 includes: the driving module 220 converting the drive current (Idrv) to a drive voltage (Vdrv); the driving module 220 converting the drive voltage (Vdrv), which is in an analog format, into a digital format; and determining the second biomolecule characteristic using the drive voltages (Vdrv).

In this embodiment, method 1300 further includes: the switch 1210 receiving a control signal (CS2) and selectably connecting the voltage generator 410 and an electrode layer 150b or 1050b to each other; the voltage generator 410 receiving an input signal (IN4) and generating a reference voltage (Vref2), applied to the electrode layer 150b or 1050b, that corresponds to the input signal (IN4); the switch 1220 receiving a control signal (CS3) and selectably connecting the sensing module 420 and an electrode layer 150c or 1050c to each other; the sensing module 420 generating a bias voltage (Vbias3) applied to the electrode layer 150c or 1050c, respectively, that results in a sensed voltage between the electrode layer 150b or 1050b and the electrode layer 150c or 1050c; the sensing module 420 detecting a sense current (Isense) through the electrode layer 150b or 1050b and the electrode layer 150c or 1050c, respectively, that is associated with the sense voltage and a corresponding resistance of the nanopore layer 140 or 1040 respectively; the sensing module 420 converting the sense current (Isense) to a sense voltage (Vsense); the sensing module 420 converting the sense voltage (Vsense), which is in an analog format, into a digital format; and one or more characteristics of the first/second biomolecule are determined using the sense voltages (Vsense).

Figure 14:
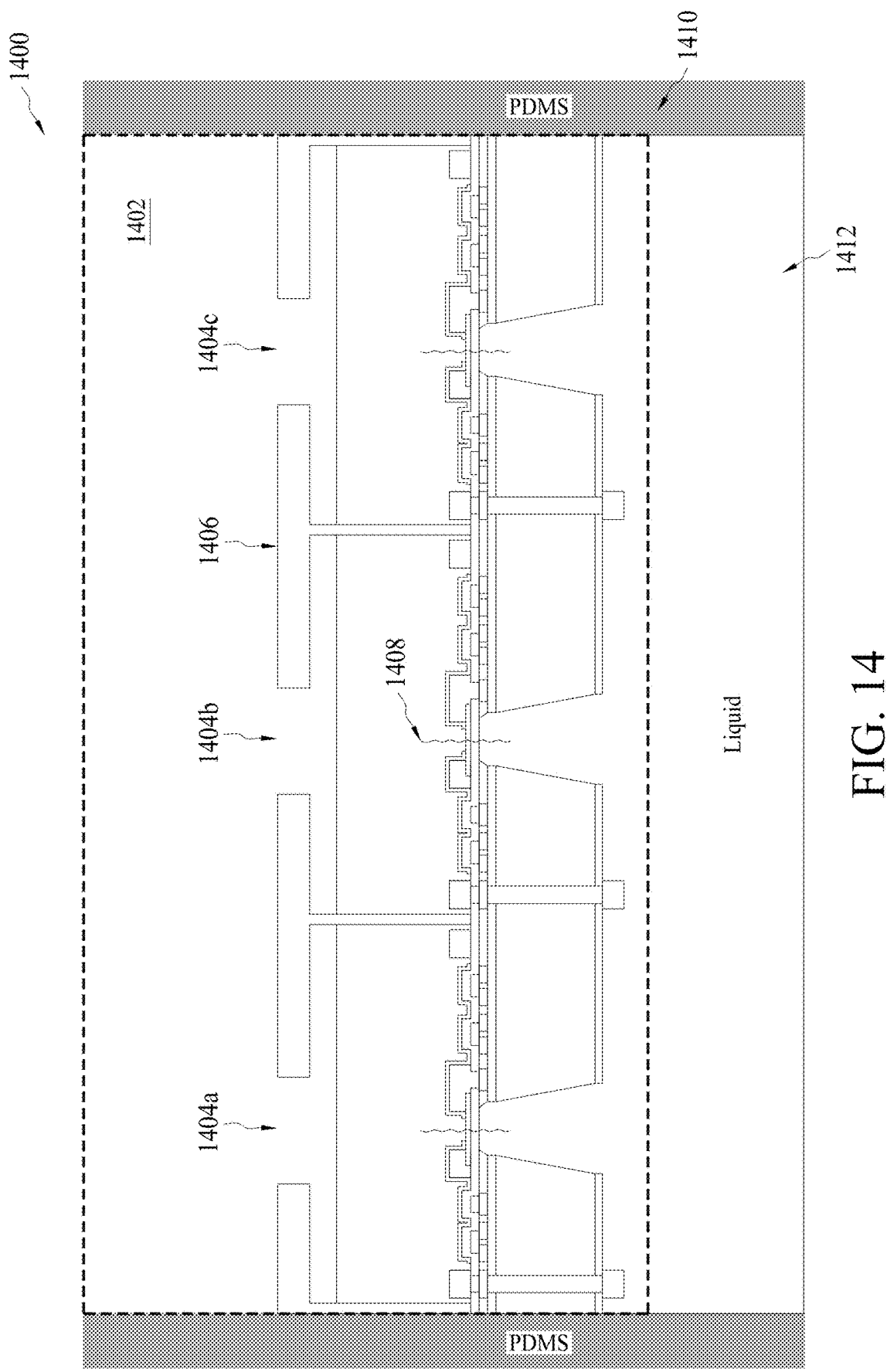
FIG. 14 illustrates an exemplary nanopore cell array in accordance with some embodiments.

FIG. 14 illustrates a PDMS (polydimethylsiloxane) measurement cell 1400 that may be utilized for various biosensors, for example a portable handheld biosensor, comprising (as illustrated) three semiconductor devices, which in embodiments may include semiconductor device 100, in each of cell 1404a, 1404b, 1404c. It will be appreciated that the measurement cell, e.g. a microfluidic chip such as microfluidic chip 196, may be formed of any material suitable for microfluidic applications, for example glass, silicon or other suitable polymers. An array of nanopore cells 1402 includes a plurality of nanopore cells 1404a, 1404b, 1404c separated from each other by silicon caps, e.g. silicon cap 1406. Each nanopore cell 1404a, 1404b, 1404c includes a semiconductor device 100 with integrated nanopore device 140.

While the exemplary array of nanopore cells 1402 is illustrated with three exemplary nanopore cells 1404a, 1404b, 1404c, any number of nanopore cells may be used without exceeding the scope of this disclosure. Each nanopore cell 1404a, 1404b, 1404c is electrically separated from each other by the silicon caps 1406, and each nanopore (e.g. 140A) in each nanopore cell 1404a, 1404b, 1404c is formed in situ, electrically, and independently of the other, according to the present disclosure. The nanopore cell array 1402 is inserted into the PDMS measurement cell 1400 with microfluidic channels (e.g. 194, not particularly depicted in FIG. 14) that feed into and form a reservoir 1410 for containing a working fluid 1412 in contact with either side of the nanopore cell array 1402 (which may be an embodiment of array 180). Each nanopore cell, e.g. 1404b, may individually sense the properties of individual biomolecules, e.g. biomolecule 1408, present in or introduced into the fluid 1412, as it passes through the nanopore cell's 1404b nanopore (e.g. nanopore 140A). In embodiments sensing circuitry and the decoding circuitry, e.g. circuitry 110A, 110A1, 200, 400, formed in semiconductor layer 110 of each semiconductor device 100 of each nanopore cell 1404a, 1404b, 1404c, are localized in each nanopore cell, e.g. 1404b, each nanopore cell is able to reliably and accurately report its sensed biomolecule characteristics (e.g. based on varying resistance or capacitance of the nanopore as a biomolecule passes through the nanopore, e.g. 140), to a biosequencing device.

Figure 15:
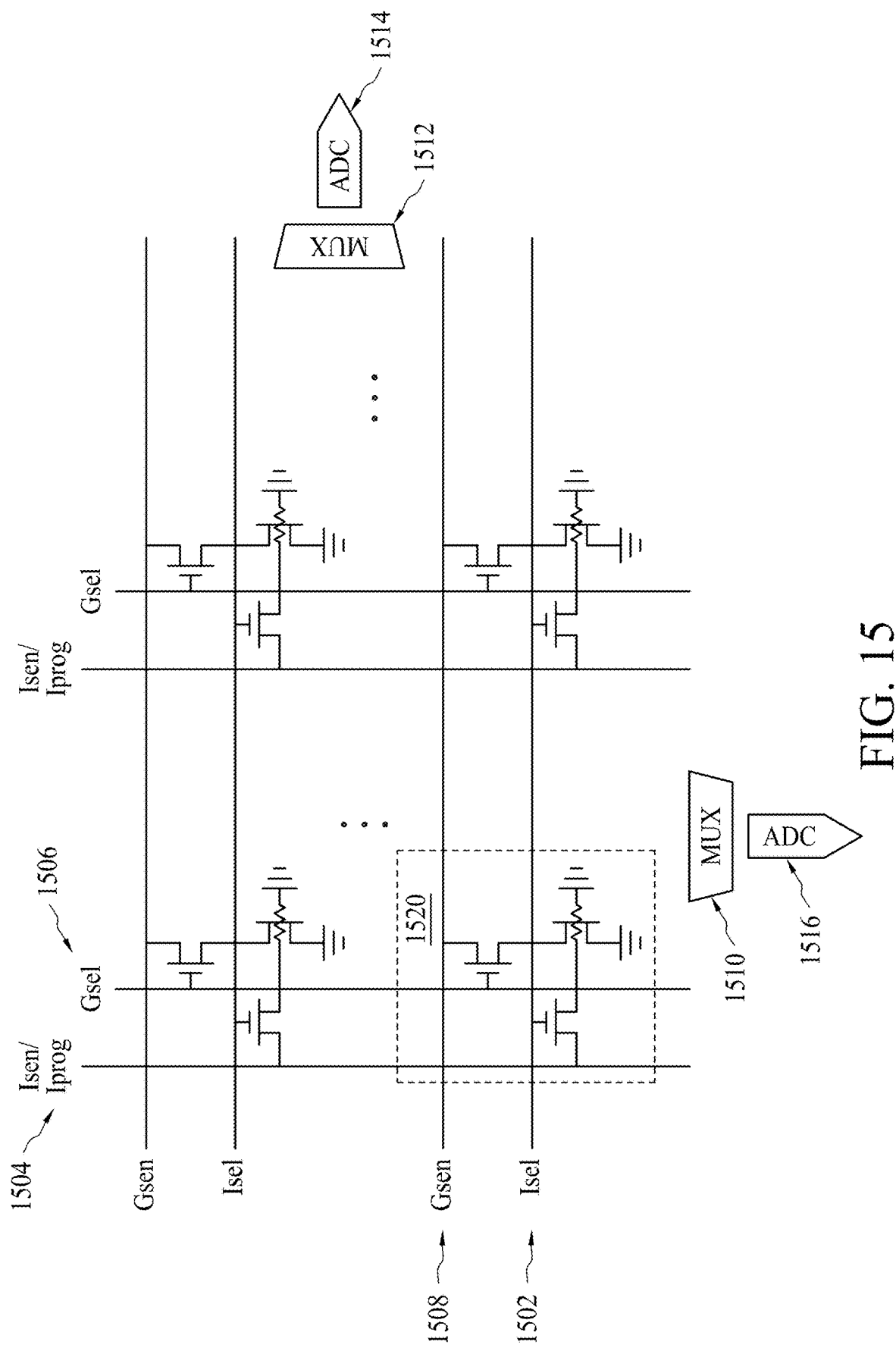
FIG. 15 illustrates a schematic of an integrated circuit for controlling an array of semiconductor based biomolecule sensor devices in accordance with some embodiments.

FIG. 15 illustrates a simplified device schematic for controlling the programming and sensing of an array of nanopore cells, e.g. array 1402 according to various embodiments. Each nanopore cell device may include an embodiment of semiconductor device 100, and may receive control signals via control circuitry formed in semiconductor device layer 110, or applied to IO electrodes 170A, 170B. Each nanopore cell response to, among other signals, four control signals Isel 1502, Isen/Iprog 1504, Gsel 1506, and Gsen 1508. Isel 1502, for a given combination nanopore/semiconductor IC device 1520, which may be device 100, enables selection of a respective ion channel signal (e.g. a signal associated with $i_B$ in path 155). Isen/Iprog 1504 provides either a programming voltage for forming a nanopore (as described herein in reference to FIGS. 1A-1D 2A-2B, 3A-3C, 4, 5), or Isen/Iprog 1504 activates a sensing current which may be selected by mux 1510 in order to convert a sensed current to a digital signal for output to an external device (like a portable biosensor, or other type of biosensor). Alternatively, Gsel 1506 may be asserted, which selects the membrane channel, (e.g. channel associated with $i_T$), and Gsen 1508 may provide a sensing signal that may be selected, by mux 1512, for analog to digital conversion by ADC 1514 for transmission to an external device for processing, e.g. via output 198 to a biomolecule characterization device.

FIGS. 16A, 16B, 16C illustrate various aspects of embodiments of an exemplary nanopore cell array 1630 according to various embodiments. FIG. 16A illustrates a cross section of a single nanopore cell 1600 and includes an equivalent circuit 1610 for sensing a biomolecule. Nanopore cell 1600 includes a semiconductor device, e.g. a semiconductor device 100, as a sensor device (e.g. 2D transistor 140 sensor with integrated sensing circuitry) and sensing circuitry e.g. a first and second circuit 200, 400 formed in a semiconductor device layer 110. A cis program-and-sense ring 1602 (e.g. an electrode such as an embodiment of electrode 150A) encircles the nanopore 140A and nanopore layer 140 on the cis side of a membrane 1606 (e.g., a graphene transistor, or a nanopore layer), and a trans program-and-sense-ring 1604 (e.g. an electrode such as an embodiment of electrode 620) encircles the nanopore and nanopore layer 140 on the trans side of a membrane 1606, thereby providing contacts between, e.g., first circuit 200 and the fluid present on each side of the membrane 1606. This contact allows a control circuit, e.g. first circuit 200, to establish a voltage difference across a membrane 1606 having a nanopore 1620 through which a biomolecule 1608 may pass. As biomolecule 1608 passes through nanopore 1620 the resistance and capacitance of the ionic circuit varies, which causes a varying voltage to appear across the membrane 1606. This varying voltage causes a varying current between the membrane source 1614 and the membrane drain 1612 (as illustrated by equivalent circuit 1610), which may be converted into a digital representation by local CMOS circuitry, e.g. in circuit layer 110, for transmission to an external device for further processing. The membrane drain 1612 and membrane source 1614 may be electrically coupled to other cells in the array 1630, and to control circuitry (not shown in detail), through line 1622 and line 1624 respectively. In embodiments signals Gsen 1508 and Gsel 1506 may be provided to the membrane transistor through lines 1622, 1624 (in a manner analogous to a word line or a bit line in a memory cell array). Similarly, signals Isel 1502 and Isen/Iprog 1504 may be provided to the ionic channel by way of trans prog and sense ring 1604 and cis prog and sense ring 1602.

As in the embodiments illustrated in FIG. 16C a trans ring of each individual nanopore cell 1600 is couple to a transring of each other nanopore cell, and likewise each cisring is coupled together, in this way each a solutions surrounding each nanopore is maintained at a similar potential during application of drive or sensing voltages. Additionally, control lines GD 1622 and GS 1624 for controlling currents applied across each nanopore device, e.g. nanopore cell 1600, may be routed to a single control circuit that is separate from each cell's sensing circuitry, e.g. sensing circuitry disposed in a semiconductor layer 1650, local to each nanopore cell 1600, and which may be independently coupled to a transchamber by TSV 1640. In this way, control circuit of the array, e.g. control circuit 110B, may be separate and distinct from sensing circuitry formed in a semiconductor layer, e.g. 1650.

Figure 17:
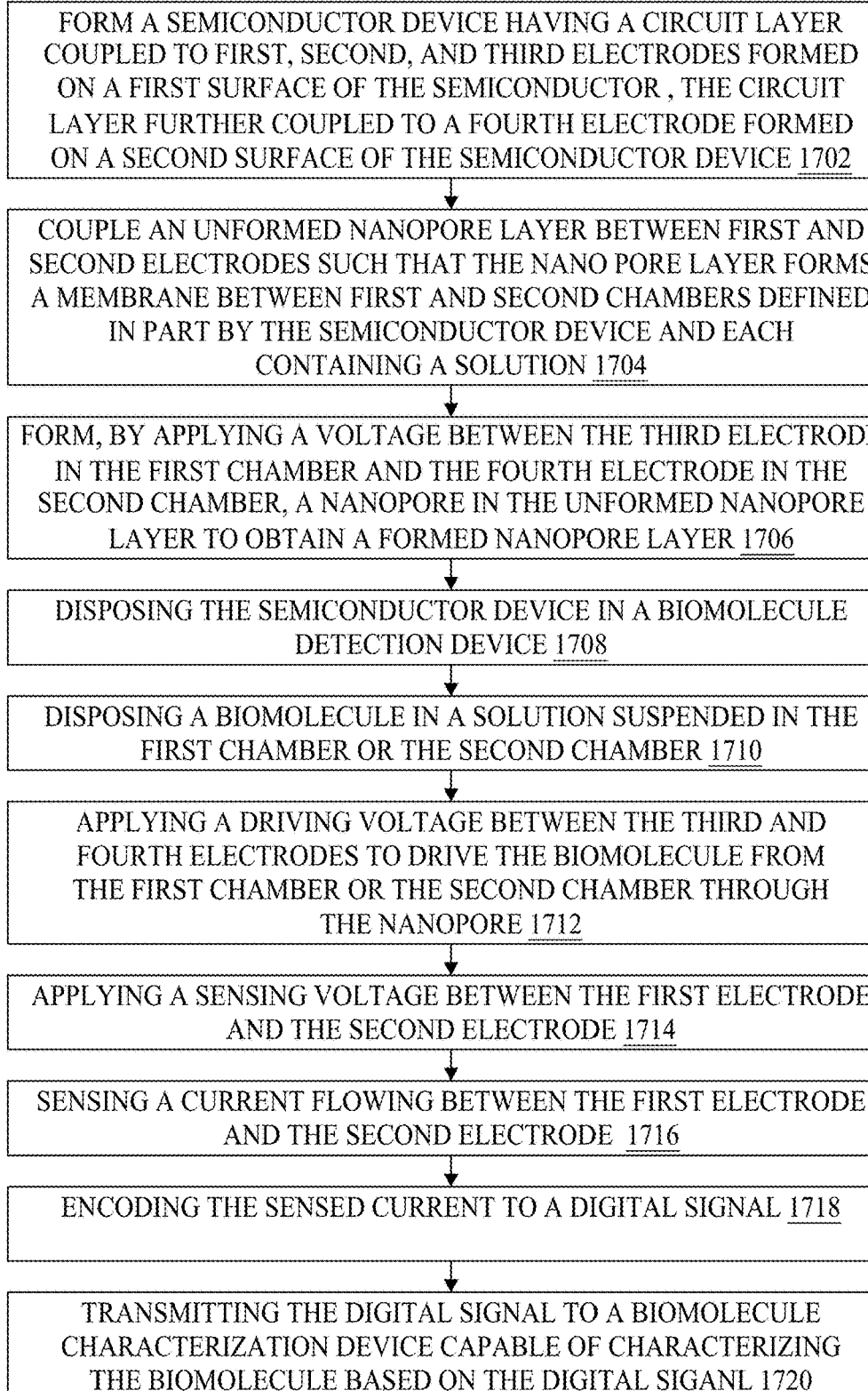
FIG. 17 is a flow chart illustrating an exemplary method of forming a nanopore in accordance with some embodiments.

FIG. 17 is a flow chart illustrating an exemplary method 1700 of determining a biomolecule characteristic in accordance with some embodiments. At step 1702 a semiconductor device, e.g. 100, is formed having a circuit layer, e.g. 110, coupled to first, second, and third electrodes, e.g. 150A, 150B, 150C, formed on a first surface of the semiconductor, the circuit layer, e.g. 110, further coupled to a fourth electrode, e.g. 620, formed on a second surface of the semiconductor device. At 1704, an unformed nanopore layer (having no nanopore, e.g. nanopore device 140 prior to pore formation) is coupled between the first and second electrodes, e.g. 150B, 150C, such that the nanopore layer, e.g. 140, forms a membrane between first and second chambers, e.g. 130A, 130B, defined in part by the semiconductor device, e.g. 100 and each chamber, e.g. 130A, 130B, containing a solution, e.g. 800. At step 1706, a voltage is applied between the third electrode, e.g. 150A, in the first chamber and the fourth electrode, e.g. 620 in the second chamber, thereby forming a nanopore, e.g. 140A, in the unformed nanopore layer to obtain a formed nanopore layer, e.g. 140. At 1708 a semiconductor device, e.g. 100, is disposed in a biomolecule detection device, e.g. microfluidic chip 196. And a biomolecule is disposed, at 1710, in a solution suspected in a first chamber, e.g. 130A, or a second chamber, e.g. 130B. A driving voltage is applied, in step 1712, between the third, e.g. 150A, and fourth electrodes, e.g. 620, to drive the biomolecule from the first chamber or the second chamber through the nanopore, e.g. 140. A sensing voltage is applied between the first electrode, e.g. 150A, and the second electrode, e.g. 150B, at 1714, and at 1716 a current flowing between the first and second electrodes is sensed, e.g. by an integrated circuit formed in circuit layer 110. The sensed current is encoded in a digital signal at 1718, and at 1720 the digital signal is transmitted, e.g. via output 198, to a biomolecule characterization device capable of characterizing the biomolecule based on the digital signal.

From the above, the semiconductor device of the present disclosure includes a circuit layer and a nanopore layer. The circuit layer includes a circuit configured to drive a biomolecule through a pore in the nanopore layer and to detect a drive/sense current associated with a resistance of the nanopore layer. The circuit is a driving/sensing circuit that is built-in to the semiconductor device such that parasitic capacitances associated with the drive/sense currents detected by the circuit are reduced. Thus, a relatively accurate biomolecule characteristic can be obtained from the drive/sense currents provided by the semiconductor device.

Devices and methods in accordance with this disclosure provide many benefits including enabling an integrated semiconductor nanopore process structure. This semiconductor nanopore process structure may contain CMOS transistors, interconnects, thin film membranes for forming nanopores, a liquid chamber in which formation occurs, and programming electrodes. A nanopore may be formed by in-silicon (or generally in situ) by programming circuits. An in-silicon sense amplifier circuit and signal processing circuits, such as ADC, DAC, IVC, may be integrally formed with a sensing device, and may be used to digitize the signal and to communicate the signal to an external computing device. To digitize the signal means to convert an analog sensed signal into a digital form, e.g. a 16-bit, or 32-bit, or 64-bit word, prior to transmitting the sensed signal to an external computing device. One of skill in the art will appreciate any digital encoding of the analog signal may be employed. Thus, the signal to noise ratio is significantly improved at the receiving device, e.g. a biomolecule characterizing device. The membrane, e.g. nanopore layer 140, may be formed using 2D FETs such as Graphene FETs or MOS2 FETs. The devices and methods disclosed herein are useful for DNA sequencing. For forming nanopore cell boundaries, silicon caps with pre-drilled holes may be bonded to a silicon substrate to provide liquid isolation and thereby isolate each cell.

The semiconductor device of the present invention provides many benefits. Devices in accordance with this disclosure are useful in handheld biometric devices. For example, a handheld biological molecule detection and characterization device would employ an integrated semiconductor nanopore process structure. Because of its integrated nature, the nanopore sensor SNR is greatly reduced by eliminating noise introduced by long sensor wires, thus enabling a reliable sensing device. The semiconductor nanopore process structure contains CMOS transistors, interconnects, a thin film nanopore, a liquid chamber formation, and program electrodes as described above. The nanopore is formed by in-silicon programming circuits as described above. Additional, in-silicon sense amplifier circuits and signal processing circuits, such as analog-to-digital converters, or digital to analog converters, or current to voltage signal converters. These components are used to digitize the signal and communicate the digitized signal to the handheld biological molecule detection and characterization device. In embodiments, 2D FETS such as graphene FETS or MOS2 FETs are used for biological detection and sequencing purposes. In embodiments, an array of semiconductor nanopore process structures are employed; each semiconductor nanopore process is isolated from others in the array by a cavity structure having silicon caps with pre-drilled holes which may be bonded to silicon substrate to provide liquid isolation.

In an embodiment, a semiconductor device comprises a circuit layer and a nanopore layer. The nanopore layer is formed on the circuit layer and is formed with a pore therethrough. The circuit layer includes a circuit unit configured to drive a biomolecule through the pore and to detect a current associated with a resistance of the nanopore layer, whereby a characteristic of the biomolecule can be determined using the currents detected by the circuit unit.

In another embodiment, a method of manufacturing a semiconductor device comprises forming a circuit layer, transferring a nanopore layer from a source substrate to the circuit layer, and forming a chamber on the circuit layer such that the nanopore layer is disposed in a chamber cavity in the chamber.

In another embodiment, a method comprises filling a chamber formed on a circuit layer with a chemical solution and enabling a circuit of the circuit layer to drive a biomolecule from the chamber through a pore in a nanopore layer.

In embodiments, an array is formed by metal and source/drain as interconnects. A membrane transistor is connected together to form integrated circuits. The programing, sensing and driving electrodes are formed by metal rings around each cell on both the cis side and trans side of the membrane. A cell to be programmed is selected by a CMOS circuit addressing signal in a similar manner as techniques employed in SRAM or other memory addressing methods. A duration of a program pulse is controlled electronically by integrated decoding circuits as described herein. A soaking signal, after programming, is also controlled electronically to provide soaking pulses having soaking pulse widths for a number of pulse. A pore is formed during programming, and a pore's size is monitored continuously by continuous monitoring of the ion current, which is correlated with the nanopore size as described herein (e.g. correlated by prior direct measurement). Once a specified ion current is reached, a desired pore size is achieved and soaking of the pore is terminated. A to-be-detected biomolecule, e.g. a particular DNA strain, is then deposited in a cells fluid and a bias voltage is applied (smaller than programming and soaking voltage) to drive the biomolecule through the nanopore. While the DNA strain passes through the nanopore, the ion current from cis and trans terminals will change according to the type of nucleotides. At the same time, the membrane transistor source/drain is affected significantly, and a measured current is larger and of better SNR quality than in known methods. The membrane transistor may be a GNR transistor. The membrane transistor current $i_T$ and the ion current through cis-trans terminal may be compared for more accuracy detection.

In embodiments, disclosed process technology combines SOI CMOS technology, MEMS technology and Graphene Nano-Ribbon transistor technology. This combination may be employed to form nanopore cells and sensing components, e.g. first circuit 200 and second circuit 400 in semiconductor layer 110 as CMOS circuits, e.g. 110A, 110A1, according to the following summarized process, more fully described below. First, top size silicon and through substrate vias (TSV) are formed. Then SOI CMOS transistors are formed, e.g. in circuit layer 110. Then thin SIN is deposited over the circuit layer 110. A 2D transistor (e.g. graphene) layer is then transferred onto a surface of the SIN and graphene/metal contacts and silicon contacts are formed coupling the 2D transistor layer 140 to the circuit layer 110 components. Backside silicon metal is formed, and etched in order to form a cavity (e.g. 130B). Backside SiN is then patterned or etched as desired, and finally silicon caps are formed and then bonded to sensor wafers.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A biomolecule sensing device comprising at least one semiconductor device, each semiconductor device including:
    a semiconductor circuit layer; and
    a nanopore layer disposed above the circuit layer and coupled to a circuit unit within the circuit layer by semiconductor device routes, the nanopore layer having a nanopore therethrough, wherein the circuit unit is configured to drive a biomolecule through the pore and the circuit unit is configured to detect a current associated with a resistance or a capacitance of the nanopore layer, whereby a characteristic of the biomolecule can be determined using the current detected by the circuit unit, wherein the nanopore is a liquid gated transistor.

2. The semiconductor device of claim 1, wherein the circuit unit within the circuit layer is coupled to an electrode for sensing a current that varies in proportion to the resistance or the capacitance, the resistance or capacitance varying as the biomolecule passes through the pore, the semiconductor device further comprising:
    a current to voltage converter formed within the circuit layer for converting a sensed current to a voltage; and
    an analog to digital converter coupled to the current to voltage converter for digitizing the voltage for transmission to a biological characteristic detection system.

3. The semiconductor device of claim 1, further comprising a chamber defining a chamber cavity therein that extends through the pore and the circuit layer and that is configured to receive a chemical solution.

4. The semiconductor device of claim 3, further comprising:
    a first electrode disposed above the circuit layer,
    a second electrode formed below the circuit layer opposite the first electrode such that the first electrode and the second electrode are disposed within portions of the chamber separated by the semiconductor layer, the nanopore layer and the pore; and
    a wafer between the circuit layer and the electrode layer, wherein the chamber cavity further extends through the electrode layer and the wafer, wherein the current detected by the circuit unit passes from the electrode to the electrode layer through the pore when the chamber contains a solution, or wherein the current detected by the circuit unit passes through the nanopore layer.

5. The semiconductor device of claim 4, wherein the nanopore layer comprises graphene, the nanopore layer has a thickness of between 1 nanometer and 5 nanometers, the pore therethrough having a diameter of 10 nanometers.

6. The semiconductor device of claim 1, further comprising a silicon nitride layer having an aperture, the nanopore layer disposed upon the silicon nitride layer such that the pore overlaps the aperture.

7. The semiconductor device of claim 6, wherein the nanopore layer is disposed in a chamber cavity that extends through the pore to a lower chamber cavity, each of the upper chamber cavity and the lower chamber cavity containing a chemical solution for suspending biomolecules to be driven by the circuit unit.

8. The semiconductor device of claim 6, further comprising an electrode layer disposed in the upper chamber cavity, the electrode layer formed over the circuit layer, and coupled to the circuit unit.

9. The semiconductor device of claim 1, comprising two electrodes coupled to the nanopore and coupled to the circuit layer, the circuit layer comprising a circuit configured to enlarge the nanopore by applying a first voltage, the circuit layer further configured to apply a current across the nanopore layer, the circuit layer further configured to sense variations in the current indicative of the presence of a portion of a biomolecule passing through the nanopore.

10. The semiconductor device of claim 1, wherein the circuit unit is further configured to form the pore in the nanopore layer by applying a voltage to the nanopore layer.

11. The semiconductor device of claim 10, wherein the circuit unit is further configured to detect a pore current associated with a resistance of the nanopore layer, whereby a width of the pore can be estimated using the pore currents detected by the circuit unit.

12. The semiconductor device of claim 1, further comprising:
    a plurality of additional nanopore layers each including an additional pore and formed over the circuit layer in an array including the nanopore layer; and
    a plurality of silicon caps each respectively disposed over the nanopore layer or one of the plurality of additional nanopore layers and configured to retain a solution suspending a biomolecule as it passes through each respective nanopore, wherein the circuit layer includes a plurality of additional circuit units each configured to (i) separately and independently drive a respective biomolecule through a respective additional pore in a respective one of the additional nanopore layers and (ii) to detect a distinct current associated with a resistance of the respective one of the plurality of additional nanopore layers, further wherein each of the plurality of additional circuit units is configured to convert the detected distinct current to a distinct digital signal and to transmit the distinct digital signal to an external device, further wherein the silicon caps are disposed to electrically isolate each of the nanopore layer and each additional nanopore layer, and further wherein each pore is individually electrically formed by electrical pulses generated by a respective one of the plurality of additional circuit units.

13. A method comprising:
forming a semiconductor circuit layer;
disposing a nanopore layer above the circuit layer;
coupling the nanopore layer to a circuit unit within the circuit layer by semiconductor device routes, the nanopore layer having a nanopore therethrough, wherein the nanopore is a liquid gated transistor;
driving, with the circuit unit, a biomolecule through the pore;
detecting, with the circuit unit, a current associated with a resistance or a capacitance of the nanopore layer; and
determining, using the current detected by the circuit unit, a characteristic of the biomolecule.

14. The method of claim 13, wherein the circuit unit within the circuit layer is coupled to an electrode for sensing a current that varies in proportion to the resistance or the capacitance, the resistance or capacitance varying as the biomolecule passes through the pore, the method further comprising:
forming a current to voltage converter within the circuit layer;
converting, with the current to voltage converter, a sensed current to a voltage; and
digitizing the voltage for transmission to a biological characteristic detection system using an analog to digital converter coupled to the current to voltage converter.

15. The method of claim 13, further comprising receiving a chemical solution using a chamber defining a chamber cavity therein that extends through the pore and the circuit layer.

16. The method of claim 15, further comprising:
disposing a first electrode above the circuit layer; and
forming a second electrode below the circuit layer opposite the first electrode such that the first electrode and the second electrode are disposed within portions of the chamber separated by the semiconductor layer, the nanopore layer, and the pore,
wherein (i) a wafer is disposed between the circuit layer and the electrode layer, (ii) the chamber cavity further extends through the electrode layer and the wafer, and (iii) wherein the current detected by the circuit unit passes from the electrode to the electrode layer through the pore when the chamber contains a solution, or the current detected by the circuit unit passes through the nanopore layer.

17. The method of claim 13, further comprising disposing the nanopore layer upon a silicon nitride layer such that the pore overlaps an aperture of the silicon nitride layer.

18. The method of claim 17, further comprising disposing the nanopore layer in a chamber cavity that extends through the pore to a lower chamber cavity, each of the upper chamber cavity and the lower chamber cavity containing a chemical solution for suspending biomolecules to be driven by the circuit unit.

19. The semiconductor device of claim 17, further comprising:
disposing an electrode layer in the upper chamber cavity;
forming the electrode layer over the circuit layer;
coupling the electrode layer to the circuit unit;
coupling two electrodes to the nanopore and the circuit layer, the circuit layer comprising a circuit;
enlarging, with the circuit, the nanopore by applying a first voltage;
applying, by the circuit layer, a current across the nanopore layer;
sensing, by the circuit layer, variations in the current indicative of the presence of a portion of a biomolecule passing through the nanopore;
forming, by the circuit unit the pore in the nanopore layer by applying a voltage to the nanopore layer; and
detecting, by the circuit unit, a pore current associated with a resistance of the nanopore layer, whereby a width of the pore can be estimated using the pore currents detected by the circuit unit.

20. A method comprising:
forming a semiconductor circuit layer;
disposing a nanopore layer above the circuit layer;
coupling the nanopore layer to a circuit unit within the circuit layer by semiconductor device routes, the nanopore layer having a nanopore therethrough;
driving, with the circuit unit, a biomolecule through the pore;
detecting, with the circuit unit, a current associated with a resistance or a capacitance of the nanopore layer; and
determining, using the current detected by the circuit unit, a characteristic of the biomolecule;
forming, a plurality of additional nanopore layers, each including an additional pore, over the circuit layer in an array including the nanopore layer;
disposing a plurality of silicon caps each respectively over the nanopore layer or one of the plurality of additional nanopore layers;
retaining, by the plurality of silicon caps, a solution suspending a biomolecule as it passes through each respective nanopore;
driving, separately and independently by an additional circuit of a plurality of additional circuit units, a respective biomolecule through a respective additional pore in a respective one of the additional nanopore layers;
detecting, separately and independently by the additional circuit, a distinct current associated with a resistance of the respective one of the plurality of additional nanopore layers;
converting, separately and independently by the additional circuit, the detected distinct current to a distinct digital signal and to transmit the distinct digital signal to an external device;
disposing the silicon caps to electrically isolate each of the nanopore layer and each additional nanopore layer; and
forming each pore via electrical pulses generated by a respective one of the plurality of additional circuit units.

* * * * *